(12) United States Patent
Schmidt et al.

(10) Patent No.: US 8,038,885 B2
(45) Date of Patent: Oct. 18, 2011

(54) FORMATION AND ENCAPSULATION OF MOLECULAR BILAYER AND MONOLAYER MEMBRANES

(75) Inventors: Jacob J. Schmidt, Sherman Oaks, CA (US); Noah Malmstadt, Pasadena, CA (US); Tae-joon Jeon, Los Angeles, CA (US); Jason Poulos, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 538 days.

(21) Appl. No.: 12/083,410

(22) PCT Filed: Oct. 13, 2006

(86) PCT No.: PCT/US2006/040200
§ 371 (c)(1),
(2), (4) Date: Jun. 2, 2008

(87) PCT Pub. No.: WO2007/047498
PCT Pub. Date: Apr. 26, 2007

(65) Prior Publication Data
US 2009/0170118 A1    Jul. 2, 2009

Related U.S. Application Data

(60) Provisional application No. 60/726,872, filed on Oct. 14, 2005.

(51) Int. Cl.
*B01D 11/00* (2006.01)
*G01N 1/18* (2006.01)

(52) U.S. Cl. ........ 210/639; 264/4.1; 264/4.6; 264/4.7; 427/2.11; 427/2.14; 435/4; 435/7.1; 435/287.1; 435/287.2; 435/287.3; 436/86; 436/178; 436/180; 977/713; 977/717; 977/756

(58) Field of Classification Search ............ 210/634, 210/644, 645, 639; 424/429, 450, 484–492; 264/4, 4.1, 4.7, 4.6; 427/2.11, 2.14, 2.22; 425/5; 435/4, 6, 287.1, 288.5, 7.1, 287.2, 435/287.3; 514/23; 604/890.1; 436/86, 436/178, 180; 977/713, 717, 756
See application file for complete search history.

(56) References Cited

U.S. PATENT DOCUMENTS

| | | | |
|---|---|---|---|
| 6,436,905 B1 * | 8/2002 | Tonge et al. | 514/23 |
| 6,682,893 B2 * | 1/2004 | Taylor et al. | 435/6 |
| 6,699,952 B2 * | 3/2004 | Chaikof et al. | 526/277 |
| 6,846,352 B2 | 1/2005 | Yatake et al. | 106/31.58 |
| 6,846,795 B2 | 1/2005 | Lant et al. | 510/446 |
| 6,849,426 B2 | 2/2005 | Chen et al. | 435/69.1 |
| 6,852,816 B2 | 2/2005 | Lewis et al. | 526/277 |

(Continued)

OTHER PUBLICATIONS

Akeson et al., "Microsecond Time-Scale Discrimination Among Polycytidylic Acid, Polyadenylic Acid, and Polyuridylic Acid as Homopolymers or as Segments Within Single RNA Molecules," *Biophys J* 1999, 77:3227-3233.

(Continued)

*Primary Examiner* — Joseph Drodge
(74) *Attorney, Agent, or Firm* — Ballard Spahr LLP

(57) ABSTRACT

Disclosed herein are compositions, methods, and devices related to bilayer and monolayer membranes, their encapsulation in a hydrogel, and their formation. Methods of using the disclose compositions and devices are also disclosed.

26 Claims, 9 Drawing Sheets

U.S. PATENT DOCUMENTS

| | | | | |
|---|---|---|---|---|
| 7,479,483 | B2* | 1/2009 | Ponzoni et al. | 514/12 |
| 2002/0081617 | A1 | 6/2002 | Buranda et al. | 435/6 |
| 2003/0175824 | A1 | 9/2003 | Pishko et al. | 435/7.2 |
| 2005/0154374 | A1* | 7/2005 | Hunter et al. | 604/890.1 |
| 2006/0160066 | A1 | 7/2006 | Bhatia et al. | 435/4 |
| 2011/0111985 | A1* | 5/2011 | Lakey et al. | 506/18 |

OTHER PUBLICATIONS

Anrather et al., "Supported Membrane Nanodevices," *J Nanosci Nanotech* 2004, 4(1/2):1-22.

Bainbridge et al., "Voltage gating is a fundamental feature of porin and toxin beta-barrel membrane channels," *FEBS Lett* 1998, 431(3):305-308.

Bayley et al., "Stochastic sensors inspired by biology," *Nature* 2001, 413(6852):226-230.

Beddow et al., "Reconstitution of nicotinic acetylcholine receptors into gel-protected lipid membranes," *Anal Chem* 2004, 76(8):2261-2265.

Canal et al., "Correlation between mesh size and equilibrium degree of swelling of polymeric networks," *J Biomed Mater Res* 1989, 23(10):1183-93.

Costello et al., "Improved gel-protected bilayers," *Biosensors Bioelectronics* 1999, 14(3):265-271.

Favero et al., "Membrane supported lipid bilayer membranes array: preparation, stability and ion-channel insertion," *Analytica Chimica Acta* 2002, 460(1):23-34.

Ide et al., "Simultaneous Optical and Electrical Recording of a Single Ion-Channel," *Japanese J Physiol* 2002, 52:429-434.

Ide et al., "An Artificial Lipid Bilayer Formed on an Agarose-Coated Glass for Simultaneous Electrical and Optical Measurement of Single Ion Channels," *Biochem Biophys Res Commun* 1999, 265:595-599.

International Report on Patentability for PCT/US2006/040200 mailed Apr. 24, 2008.

International Search Report and Written Opinion for PCT/US2006/040200 mailed Apr. 24, 2008.

Ionescu-Zanetti et al., "Mammalian electrophysiology on a microfluidic platform,"*Proc Natl Acad Sci USA* 2005, 102: 9112-9117.

Jacobson et al., "Microchip structures for submillisecond electrophoresism" *Analytical Chemistry* (1998) 70, 3476.

Joanicot et al., "Droplet control for microfluidics," *Science* 2005, 309(5726):887-888.

Kasianowicz et al., "Characterization of individual polynucleotide molecules using a membrane channel," *Proc Natl Acad Sci USA* 1996, 93, 13770-13773.

Kazakov et al., "UV-induced gelation on nanometer scale using liposome reactor," *Macromolecules* 2002, 35(5):1911-1920.

Knoll et al., "Functional tethered lipid bilayers," *Rev Mol Biotech* 2000, 74(3):137-158.

Krishna et al. "Tethered Bilayer Membranes Containing Ionic Reservoirs: Selectivity and Conductance," *Langmuir* 2003, 19:2294-2305.

Kuhner et al., "Lipid mono- and bilayer supported on polymer films: composite polymer-lipid films on solid substrates," *Biophys J* 1994, 67(1):217-226.

Lee et al., "Solvent compatibility of poly(dimethylsiloxane)-based microfluidic devices," *Anal Chem* 2003, 75(23):6544-6554.

Lu et al., "Biophysical aspects of agar-gel supported bilayer lipid membranes: a new method for forming and studying planar bilayer lipid membranes," *Bioelectrochem Bioenergetics* 1996, 39:285-289.

Lustig et al., "Solute Diffusion in Swollen Membranes .9. Scaling Laws for Solute Diffusion in Gels," *J Appl Polymer Sci* 1988, 36(4):735-747.

Matthews et al., "Design and fabrication of a micromachined planar patch-clamp substrate with integrated microfluidics for single-cell measurements," *J MEMS* 2006, 15: 214-222.

McDonald et al., "Poly(dimethylsiloxane) as a material for fabricating microfluidic devices," *Acct Chem Res* 2002, 35(7):491-499.

Meller et al., "Rapid nanopore discrimination between single polynucleotide molecules," *Proc Natl Acad Sci* 2000, 97:1079-1084.

Mueller et al., "Reconstitution of cell membrane structure in vitro and its transformation into an excitable system," *Nature* 1962, 194:979-980.

Nakane et al., "Nanopore sensors for nucleic acid analysis," *J Phys Condensed Matter* 2003, 15(32):R1365-R1393.

Naumowicz et al., "Impedance analysis of phosphatidylcholine membranes modified with gramicidin D," *Bioelectrochem* 2003, 61:21-27.

Rehak et al., "Examination of bilayer lipid membranes for 'pin-hole' character," *The Analyst* 2004, 129:1014-1025.

Sandison et al., "Rapid fabrication of polymer microfluidic systems for the production of artificial lipid bilayers," *J. Micromech Microeng* 2005, 15: S139-S144.

Sia et al., "Microfluidic devices fabricated in poly(dimethylsiloxane) for biological studies," *Electrophoresis* 2003, 24(21):3563-3576.

Sinner et al., "Functional tethered membranes," *Curr Opinion Chem Biol* 2001, 5(6):705-711.

Song et al., "Millisecond kinetics on a microfluidic chip using nanoliters of reagents," *J Am Chem Soc* 2003, 125(47):14613-14619.

Song et al., "Structure of staphylococcal alpha-hemolysin, a heptameric transmembrane pore," *Science* 1996, 274(5294):1859-66.

Suzuki et al., "Highly reproducible method of planar lipid bilayer reconstitution in polymethyl methacrylate microfluidic chip," *Langmuir* 2006, 22: 1937-1942.

Terrettaz et al., "Highly Electrically Insulating Tethered Lipid Bilayers for Probing the Function of Ion Channel Proteins," *Langmuir* 2003, 19:5567-5569.

Thorsen et al., "Dynamic pattern formation in a vesicle-generating microfluidic device," *Phys Rev Lett* 2001, 86(18):4163-4166.

Thorsen et al. "Microfluidic large-scale integration," *Science* (2002) 298, 580.

Unger et al., "Monolithic microfabricated valves and pumps by multilayer soft lithography," *Science* 2000, 288(5463), 113-116.

Wang et al., "Development of a novel solid-phase extraction element for thermal desorption gas chromatography analysis," *J Chrom A* 2004, 1035(2):277-279.

Weigl et al., "Lab-on-a-chip for drug development," *Adv Drug Delivery* 2003, 55:349-377.

Zheng et al., "Screening of protein crystallization conditions on a microfluidic chip using nanoliter-size droplets," *J Am Chem Soc* 2003, 125(37):11170-11171.

\* cited by examiner

FORMATION AND ENCAPSULATION OF MOLECULAR BILAYER AND MONOLAYER MEMBRANES

CROSSLINK TO RELATED APPLICATIONS

This application claims the benefit of priority to U.S. Provisional Application No. 60/726,872, filed Oct. 14, 2005, which is incorporated by reference herein in its entirety.

FIELD

Disclosed herein are compositions, methods, and devices related to self-assembled lipid bilayer and monolayer membranes, their encapsulation, and their formation. Methods of using the disclose compositions and devices are also disclosed.

BACKGROUND

Planar lipid bilayer membranes can provide an environment that allows single-molecule electrophysiological observations of membrane channel and pore proteins (Miller, Ion Channel Reconstitution. ed. Plenum Press: New York, 1986, p. 577). Such measurements are essential to understanding the proteins' biological function, as well as the basis of highly specific sensors capable of chemical detection (Bayley et al., *Nature* 2001, 413(6852):226-230) or potentially sequencing DNA at the single-molecule level (Kasianowicz et al., *Proc Natl Acad Sci USA* 1996, 93:13770-13773; Nakane et al., *J Phys Condensed Matter* 2003, 15(32):R1365-R1393). Unfortunately, the physical properties of current technology planar lipid bilayer membranes limit their scientific and technological application: they are difficult to form, physically weak, subject to mechanical and acoustical perturbation, and short lived.

A recent approach to address the fragility and short lifetime of lipid bilayers has been to tether them to solid surfaces (see Knoll, et al., *Rev Mol Biotech* 2000, 74(3): 137-158). Such systems combine the lipid bilayer membranes' fluidity and capacity for protein incorporation with the mechanical stability of a solid support. While electrical transport through ensembles of membrane protein channels have been measured in such systems (Favero et al., *Analyt Chim* 2002, 460(1):23-34; Naumowicz et al., *Bioelectrochem* 2003, 61:21-27) no single channels have been detected to date. This is because tethered bilayer membranes have thus far proved incapable of producing the highly insulating seals necessary for single-molecule measurements (Rehak et al., *The Analyst* 2004, 129:1014-1025), although this is improving (Terrattaz et al., *Langmuir* 2003, 19:5567-5569). Studies with tethered bilayers have also shown an inability to quantitatively measure the magnitude of incorporated channel conductances, as a result of the high in-plane resistance of the electrolyte reservoir near the substrate (Krishna et al., *Langmuir* 2003, 19:2294-2305). Furthermore, the presence of the solid surface (typically a gold electrode) makes long-term DC measurements and analyte transport across the channel problematic.

There have been attempts to use gels to support membranes. In these cases, lipid solutions were deposited on top of pre-cast gels. The resultant membranes were, however, too leaky for single channel measurement (Kuhner et al., *Biophys J* 1994, 67(1):217-226; Lu et al., *Bioelectrochem Bioenergetics* 1996, 39:285-289; Anrather et al., *J Nanosci Nanotech* 2004, 4(1/2):1-22). Ide and Yanagida formed high resistance free-standing membranes self-assembled in aqueous solution and brought them into contact with a pre-cast gel on one side (Ide et al., *Biochem Biophys Res Commun* 1999, 265:595-599; Ide et al., *Japanese J Physiol* 2002, 52:429-434). Although single channels were measured in that work, the membranes still suffered from short lifetimes. Peterson and coworkers physically sandwiched a lipid membrane between two pre-formed slabs of gel (Costello et al., *Biosensors Bioelectronics* 1999, 14(3):265-271; Beddow et al., *Anal Chem* 2004, 76(8):2261-2265). Their technique, however, has not been shown to achieve sufficiently high membrane resistances for single-molecule measurements. As noted, these techniques all rely on pre-cast gels, and they have met with limited success.

Most microfluidic approaches to ion channel analysis have adapted patch clamp technologies, which require expensive and time-consuming cell culture conditions (Ionescu-Zanefti et al., *Proc Natl Acad Sci USA* 2005, 102: 9112-9117; Matthews and Judy, *J MEMS* 2006, 15: 214-222). Furthermore, cell-based systems cannot isolate and control the environment of an ion channel to the extent possible in a cell-free system and cannot be used in ion channel-based molecular sensor applications. In this context, free-standing lipid bilayers are more appealing. In a technique commonly used to fabricate free-standing lipid bilayers in the laboratory, lipids dissolved in an organic solvent are manually "painted" over an orifice in a hydrophobic sheet submerged in an aqueous solution. This lipid solution spontaneously thins to form a bilayer membrane (Mueller et al., *Nature* 1962, 194: 979-980; White, S. H. In *Ion Channel Reconstitution*; Miller, C., Ed.; Plenum Press: New York, 1986; pp 115-139). Other approaches to microfluidic lipid membrane formation have adapted this technique to microfabricated orifices in microfluidic channels made from poly(methyl methacrylate) (Suzuki et al., *Langmuir* 2006, 22: 1937-1942; Sandison and Morgan, *J Micromech Microeng* 2005, 15: S139-S144) but suffer from a number of disadvantages. Attention from an operator is necessary to manipulate the device during membrane formation. These systems rely on a three-phase interface of lipid solution, aqueous buffer, and air; air can be problematic in microfluidic systems. Finally, the solvent in the membrane precursor solution forms an annulus around the membrane that limits the degree to which the membrane can be miniaturized (White, S. H. In *Ion Channel Reconstitution*; Miller, C., Ed.; Plenum Press: New York, 1986; pp 115-139).

In light of the important role lipid bilayers play in a vast variety of research applications, as well as the current problems associated with producing, stabilizing, and using such bilayers, what is needed in the art are methods and devices for the production, stabilization, and use of bilayers and membranes. Disclosed herein are compositions, methods, and devices that meet these and other needs.

SUMMARY

In accordance with the purposes of the disclosed materials, compositions, articles, devices, and methods, as embodied and broadly described herein, the disclosed subject matter, in one aspect, relates to compounds and compositions (e.g., bilayers and membranes) and methods for preparing and using such compounds and compositions. Also, disclosed are devices that can be used to prepare and use the disclosed compositions.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIG. 1A shows that a droplet of organic solvent with dissolved lipid is formed in an aqueous stream of fluid. Lipids are organized on the hydrophobic-hydrophilic interface (inset). FIG. 1B shows that, as solvent enters the PDMS, the two interfaces approach one another. FIG. 1C shows that only the lipid layers are left behind, forming a bilayer membrane.

FIG. 8A shows a top layer 10 (e.g., glass) in which holes are drilled or etched and three linear microfluidic channels are etched with access holes on each channel end. FIG. 8B shows a second layer 20 (e.g., glass with a thin layer of silicon deposited on its top) having a 3×3 array of holes drilled or etched into it. FIG. 8C shows a third layer 30 of a non-polar solvent-absorbing hydrophobic substance (e.g., PDMS) containing a 3×3 array of holes. FIG. 8D shows a fourth layer 40 identical to the second layer 20 in FIG. 8B with the exception that the silicon is on the bottom of the glass. FIG. 8E shows a bottom layer 50 (e.g., glass) with microfluidic channels and holes identical to the top layer 10 except rotated 90 degrees.

DETAILED DESCRIPTION

Figure 1:
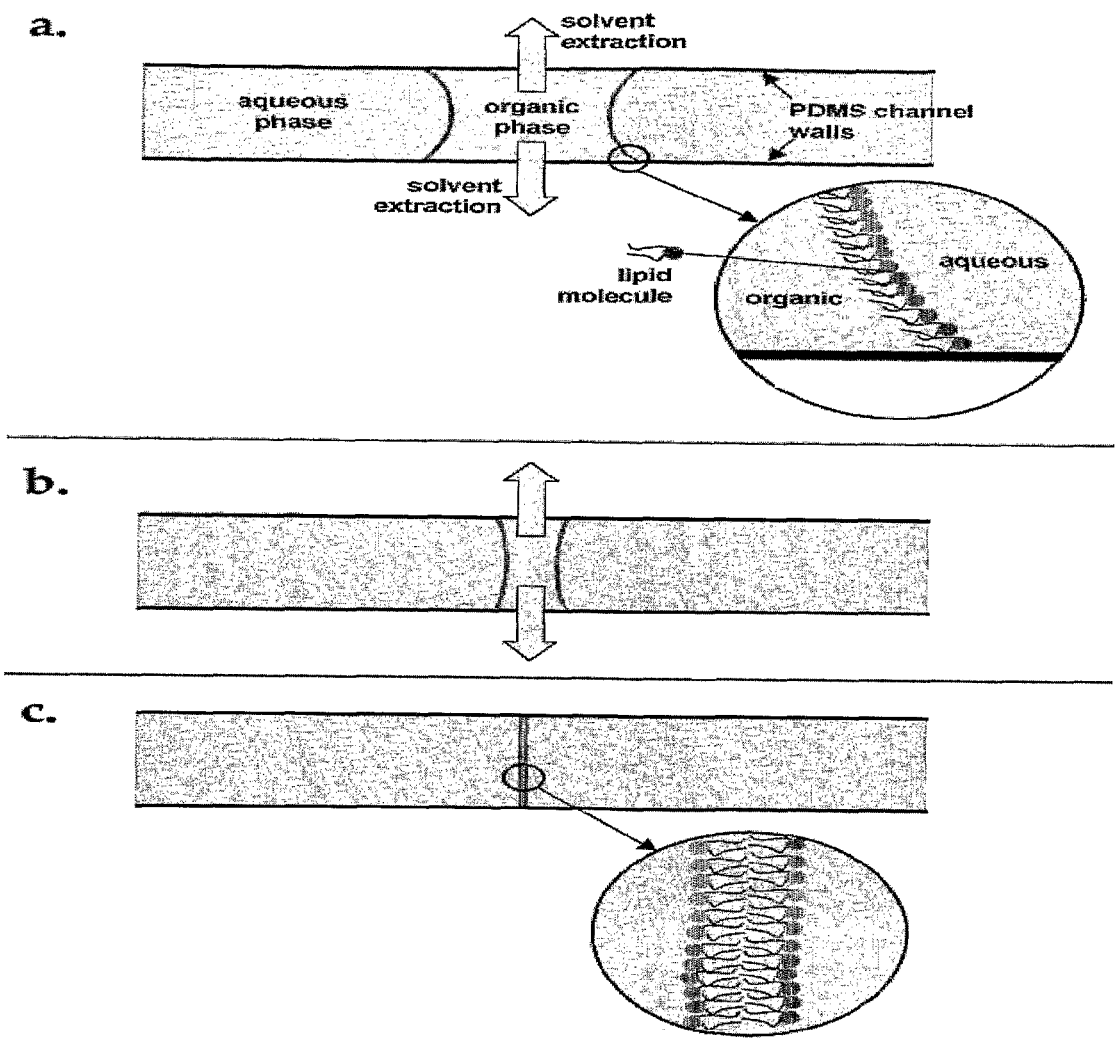
FIG. 1 is a schematic of a mechanism for bilayer formation by microfluidic solvent extraction according to the methods disclosed herein.

The materials, compounds, compositions, articles, devices, and methods described herein may be understood more readily by reference to the following detailed description of specific aspects of the disclosed subject matter and the Examples included therein and to the Figures.

Before the present materials, compounds, compositions, articles, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a compound" includes mixtures of two or more such compounds, reference to "an agent" includes mixtures of two or more such agents, reference to "the moiety" includes mixtures of two or more such moieties, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed, then "less than or equal to 10" as well as "greater than or equal to 10" is also disclosed. It is also understood that throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

A "lipid" as used herein is any molecule composed of at least one hydrophilic group and at least one hydrophobic group (i.e., an amphiphile, which is used synonymously with lipid herein).

Reference will now be made in detail to specific aspects of the disclosed materials, compounds, compositions, articles, and methods, examples of which are illustrated in the accompanying Examples.

Materials and Compositions

Disclosed herein are materials, compounds, compositions, and components that can be used for, can be used in conjunction with, can be used in preparation for, or are products of the disclosed methods, devices, and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a composition is disclosed and a number of modifications that can be made to a number of components of the composition are discussed, each and every combination and permutation that are possible are specifically contemplated unless specifically indicated to the contrary. Thus, if a class of components A, B, and C are disclosed as well as a class of components D, E, and F, and an example of a combination compound A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions and devices. Thus, if there are a variety of additional steps that can be performed it is understood that each of these additional steps can be performed with any specific aspect or combination of aspects of the disclosed methods, and that each such combination is specifically contemplated and should be considered disclosed.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Microfluidic Device for Preparing Molecular Bilayer or Monolayer Membranes

In one aspect, disclosed herein is a device for forming a bilayer or monolayer membrane. A difficulty in forming and handling membranes results from the fact that lipids and other amphiphiles spontaneously form or segregate to interfaces between hydrophobic and hydrophilic phases. Such biphasic systems can be difficult to handle using traditional lab-scale techniques, which in general rely on processes in homogenous solutions. However, recent research has shown that microfluidic channels can be used for establishing and controlling phase interfaces. In 2001, Thorsen et al. demonstrated the formation of droplets of water in a flowing microfluidic oil stream (*Phys Rev Lett* 2001, 86(18):4163-4166). Similarly, the Ismagilov group has used droplets of water flowing in an immiscible organic medium to form controlled nanoliter reaction chambers for the study of protein crystallization (Zheng et al., *J Am Chem Soc* 2003, 125(37): 11170-11171) and chemical reaction kinetics (Song et al., *J Am Chem Soc* 2003, 125(47):14613-14619).

The devices, as well as the methods, disclosed herein comprise a biphasic flow configuration in combination with solvent extraction from an organic phase. As shown in FIG. 1, lipids or other amphiphiles dissolved in the organic phase can organize at the phase interface, driven by the minimization of unfavorable interactions between hydrophilic head groups and nonpolar organic solvent. As solvent is extracted from the organic phase, tail groups can be brought together to form a bilayer membrane. In a likewise manner, monolayer membranes can be formed when the amphiphile is a multi-block copolymer containing a hydrophilic-hydrophobic-hydrophilic moiety. In one exemplary aspect, solvent extraction can be accomplished using the constituent material of the microfluidic channel (e.g., a hydrophobic substance such as poly- (dimethylsiloxane) (PDMS)). While PDMS has been used to construct microfluidic devices for handling aqueous solutions (McDonald et al., *Acct Chem Res* 2002, 35(7):491-499; Sia et al., *Electrophoresis* 2003, 24(21):3563-3576), it is a highly nonpolar polymer into which nonpolar organic solvents tend to partition (Lee et al., *Anal Chem* 2003, 75(23):6544-6554). In fact, its affinity for organic solvents is so great that PDMS has been used to extract organic solvents from chromatography samples (Wang et al., *J Chrom* 2004, 1035(2):277-279).

The disclosed devices can be used for bilayer and monolayer membrane formation. In one example, the disclosed device can comprise a substrate, at least one first microfluidic channel defined in the substrate, and at least one second microfluidic channel defined in the substrate. In one aspect, at least one first microfluidic channel is connected to and is in communication with at least one second microfluidic channel. In a further aspect, at least one of the first and second microfluidic channels can comprise a hydrophobic substance. It is contemplated that the disclosed devices are not limited by the particular order, identity or priority of the respective first or second microfluidic channels, i.e., the identifiers "first" and "second" are merely arbitrary and are used herein to simply distinguish one microfluidic channel or group of channels from the other. No connotation of order is intended as any order is contemplated.

In an additional aspect, the components of the disclosed device should be compatible with the particular lipids, amphiphiles, analytes, and reagents with which the device is to be used and come in contact with. For example, the device can be used to form and analyze bilayer and monolayer membranes; hence, the device should not react with, degrade, or have any deleterious impact on the particular compounds that are to be analyzed. In a further aspect, the device should be stable towards and resist degradation from typical solvents used in biological chemical applications and preparations.

Substrate

As noted above, the disclosed devices comprise a substrate, which typically functions as a support or matrix for the microfluidic channels. In one aspect, the substrate of the device can be made of material that is readily commercially available and/or can be prepared by methods known to one of ordinary skill in the art. The substrate can be made from any material that does not affect, interfere with, or in anyway diminish the devices particular end use purposes. Thus, substrate materials that could react with, change, alter, or degrade a desired lipid or analyte for which the device is being used should be avoided.

Suitable materials for the substrate can comprise, and are not limited to, silicon (single crystal or polycrystalline), coatings on silicon (e.g., silicon nitride), silicone, glass, quartz, platinum, stainless steel, copper, aluminum, nickel, gold, titanium, ceramics, diamond, and/or plastics (e.g., high-density polyethylene, polyethylene terephthalate, polymethyl-methacrylate, polystyrene, cellulose acetate, polyimide, and/or polycarbonate). In a specific example, the substrate can comprise polydimethylsiloxane.

Additional substrates can comprise, and are not limited to, polyalkylene polymers and copolymers, fluorocarbon polymers and copolymers, polyester polymers and copolymers, polyether polymers and copolymers, silicone polymers and copolymers, and polyurethane polymers and copolymers. Other polymers that can be used comprise, and are not limited to, polyethylenes, polypropylenes, polytetrafluoroethylenes, poly(tetrafluoroethylene-co-hexafluoropropenes), modified ethylene-tetrafluoroethylene copolymers, ethylene chlorotrifluoroethylene copolymers, polyvinylidene fluorides, polyethylene oxides, polyethylene terephthalates, silicones, polyurethanes, polyether block amides, and polyether esters.

The particular substrate to be used in a particular device can be determined by one of skill in the art based on the particular end use purposes of the device.

In certain exemplary aspects, the substrate can have or be prepared from multiple layers. For example, the substrate can comprise more that one, more than two, more than three, more than four, or five or more layers. In such examples, the respective first and second microfluidic channels of the device can be defined in or through one or more of the various layers of the device. That is, a microfluidic channel of the device can be in a single layer and, optionally, connected to one or more other microfluidic channels in an adjacent layer. Alternatively or additionally, a microfluidic channel of the device can be formed from multiple layers by aligning a pore, hole, or channel in one layer with a pore, hole, or channel in an adjacent layer. By having such an alignment, a fluid can flow through the various layers of the substrate in a microfluidic channel that is defined by the respective pores, holes, or channels in those layers.

By having a substrate comprising one or more layers, one can fine tune various aspects of membrane formation. For example, certain layers can define channels or wells for excess fluid, which function as reservoirs. Using multiple layers with multiple channels or wells can allow one to select various fluids, solvents, lipids, amphiphiles, analytes, and the like, or various concentrations of such compositions by choosing one layer or another. Still further, various layers with openings of different sizes can be used to create microfluidic channels of varying sizes and thus allow the operator to selectively alter the flow rates of the fluid therethrough a selected microfluidic channel. In a further aspect, one or more of the layers of the substrate can be made of different materials, such that the fluid passing through the microfluidic channel in the substrate can be brought into contact with the different materials. For example, one of the layers of the device can be a hydrophobic substance, which can extract organic solvent as the fluid passes through and comes in contact with that particular layer.

Microfluidic Channels

As discussed above, the disclosed devices comprise one or more first and second microfluidic channels that are defined on or in a substrate. As used herein, microfluidic channels are fluidic channels with at least one dimension (width, height, and length) on the micrometer scale (i.e., greater than about 1 µm but less than about 1 mm). Incorporating microfluidic channels on or in a substrate can be performed by conventional photolithographic, etching, deposition, embossing, laminar assembly, photoablation, and/or molding techniques (see Thorsen, T., Maerkl, S. J., Quake, S. R., *Science* (2002) 298, 580; Jacobson, S. C., Culbertson, C. T., Daler, J. E., and Ramsey, J. M., *Analytical Chemistry* (1998) 70, 3476, which are incorporated herein at least for their teachings of forming microfluidic channels).

It is contemplated that the disclosed microfluidic channels can have a variety of shapes, which can depend on the particular composition of the channel and substrate, the particular lipids, the desired size and shape of the bilayer or monolayer membrane, preference, and the like. For example, one or more of the disclosed microfluidic channels can have a width of from about 0.1 to about 1000 µm, from about 10 to about 500 µm, from about 50 to about 250 µm, or from about 100 to about 200 µm. For example, one or more of the disclosed microfluidic channels can have a width of about 0.1, 0.2, 0.3, 0.4, 0.5, 0.6, 0.7, 0.8, 0.9, 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 μm, where any of the stated values can form an upper or lower endpoint when appropriate.

In another example, one or more of the disclosed microfluidic channels can have a height of from about 0.1 to about 1000 μm, from about 10 to about 500 μm, from about 50 to about 250 μm, or from about 100 to about 200 μm. In more examples, one or more of the disclosed microfluidic channels can have a height of about 0.1, 0.2, 0.3, 0.4, 0.5, 0.6, 0.7, 0.8, 0.9, 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 μm, where any of the stated values can form an upper or lower endpoint when appropriate.

In still another example, one or more of the disclosed microfluidic channels can have a length of from about 0.1 to about 50 mm, from about 10 to about 40 mm, or from about 20 to about 30 mm. In particular, one or more of the disclosed microfluidic channels can have a height of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mm, where any of the stated values can form an upper or lower endpoint when appropriate.

In one aspect, the disclosed devices can have one or more microfluidic channels having the following dimensions: 100 μm width×100 μm height×20 mm length. It is contemplated, however, that fluidic channels smaller than microfluidic channels can be used in the disclosed devices and methods. For example, nanoscale fluidic channels can be used. While not wishing to be bound by theory, it is believed that nanoscale channels (having at least one dimension from 1 nm to 1000 nm) can be used as described herein.

In a further exemplary aspect, the at least one first microfluidic channels can be used as an inlet for an organic phase (e.g., an organic solvent) and the at least one second microfluidic channels can be used as an inlet for an aqueous phase. In this aspect, the at least one first microfluidic channels is connected to and in communication with the at least one second microfluidic channels. In this way, fluid passing through the first microfluidic channel can flow into the second microfluidic channel.

In another exemplary aspect, at least one first microfluidic channel, at least one second microfluidic channel, or both a first and second microfluidic channel can be connected to a syringe pump(s). Optionally, the syringe pumps can be controlled by computer.

In another example, the disclosed device can have multiple microfluidic channels, e.g., 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 750, 1000, or more microfluidic channels. There is no real limit to the number of channels that can be used.

Figure 8:
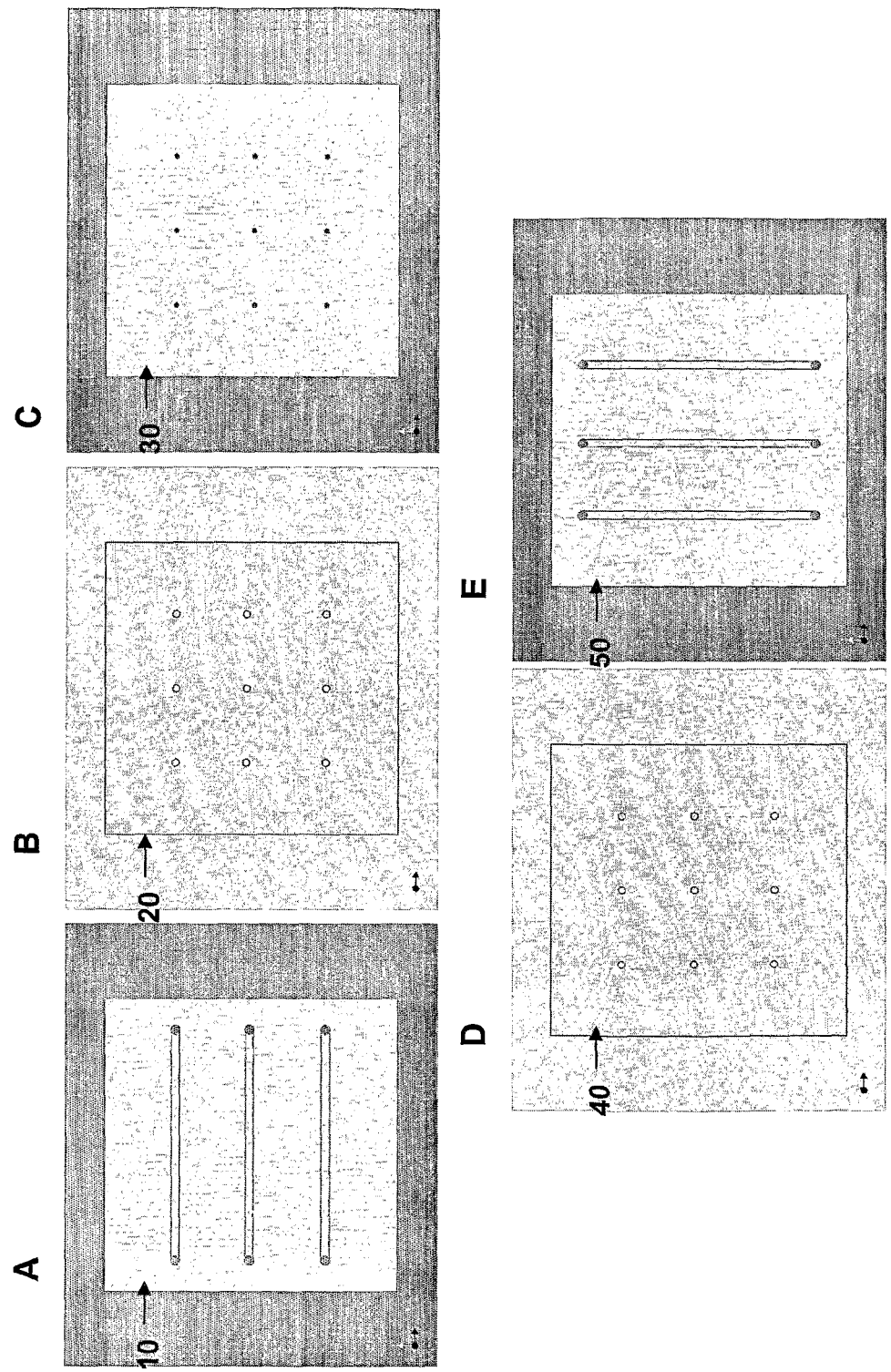
FIG. 8 is a series of schematics showing various layers of a 3×3 array device as disclosed herein.
Figure 9:
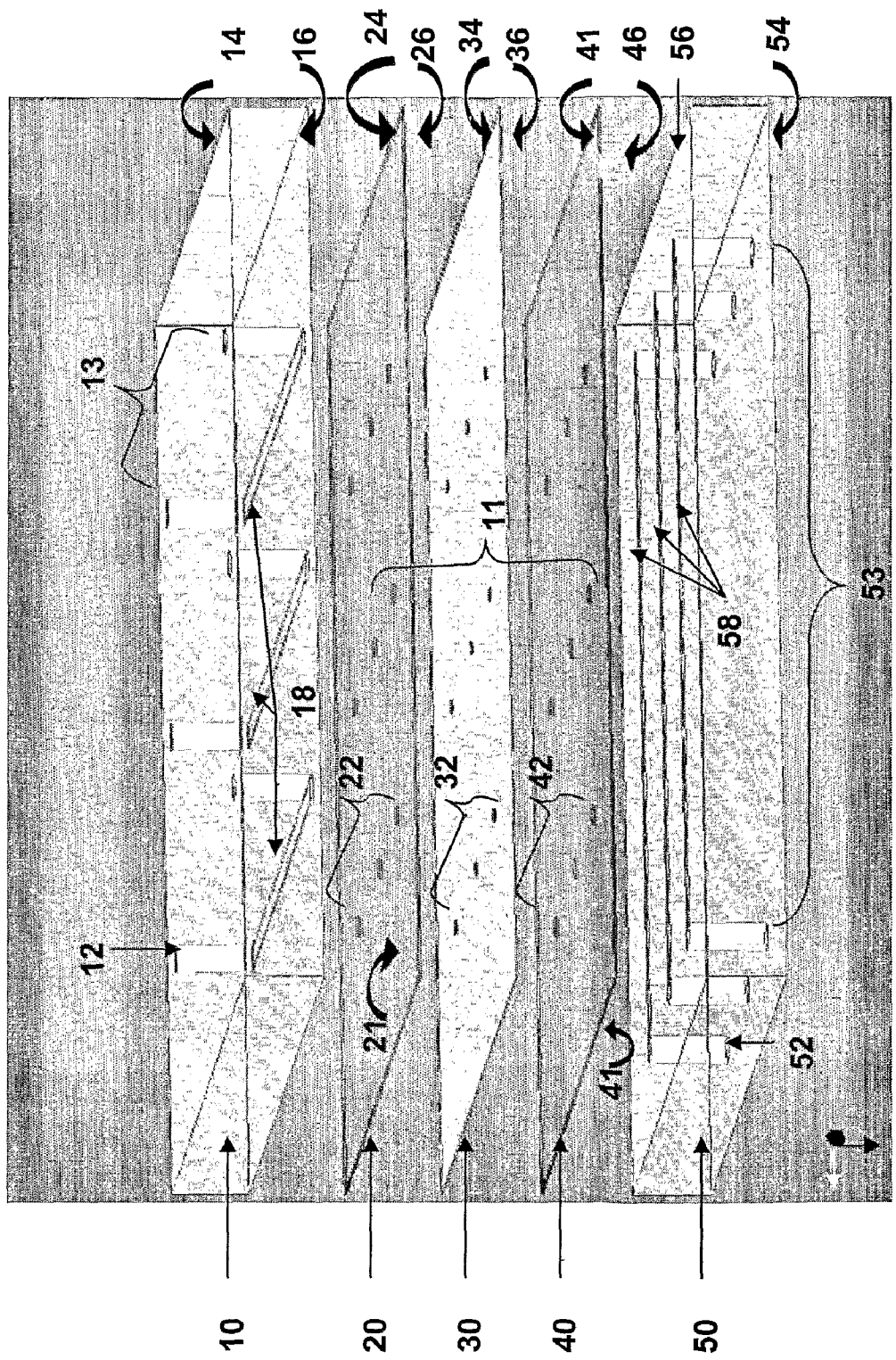
FIG. 9 is an exploded view of the 3×3 array device containing each of the layers shown in FIG. 8. The three rows of holes in the second layer 20 are in communication with each of the three channels in the top layer 10 and the three rows of holes in the fourth layer 40 are in communication with each of the three channels in the bottom layer 50. Each array of holes in the second, third, and fourth layers (20, 30, and 40, respectively) are also configured to be in communication.

In a particular example, the disclosed devices can have a plurality of microfluidic channels that are configured in an array. For example, the respective first and second microfluidic channels can be in an N×N array, where N is an integer of from 1 to 1000. An example of such a device is shown in FIGS. 8 and 9. Such a design allows for very large arrays of membranes to be simultaneously formed and individually electrically and fluidically addressed using multiplexing techniques.

Referring to FIGS. 8 and 9, both glass and hydrophobic substance (e.g., PDMS) are used, which limits the region of solvent extraction. In this example, the substrate comprises a top layer 10, a second layer 20, a third layer 30, a fourth layer 40 and a bottom layer 50. In this exemplary aspect, the top and bottom layers of glass 10, 50 have a plurality holes 12, 52 that extend therethrough the top layer from a top surface 14, 54 to the bottom surface 16, 56 of the respective top and bottom layers and three substantially linear microfluidic channels 18, 58 that are formed in the bottom surface of the respective top and bottom layers. The plurality of holes 12, 52 is configured to be in communication with the linear microfluidic channels 18, 58. In one exemplary aspect, pairs of spaced holes 13, 53 of the plurality of holes are in communication with one respective linear microfluidic channel. In another aspect, the pair of spaced holes is in communication with the spaced ends of the linear microfluidic channel. The second and fourth layers 20, 40 can be formed of glass that has a layer of silicon 21, 41 deposited on its surface facing the other glass pieces 10, 50. Each of the second and fourth layers 20, 40 has a plurality of holes 22, 42 extending from the top surface 24, 44 to the bottom surface 26, 46 of the respective layer. In one aspect, the plurality of holes 22, 42 in each of the second and fourth layers 20, 40 are configured in a 3×3 array. In this exemplary aspect, the second layer 20 is connected to the top layer 10 such that the plurality of holes 22 of the second layer are positioned in communication with the linear microfluidic channels 18 of the top layer, i.e., three of the plurality of holes of the second layer are positioned in communication with one respective linear microfluidic channel of the top layer. In this construction, each of the linear microfluidic channels 18 of the top layer 10 are in communication with three of the plurality of holes 22 of the second layer 20. As one skilled in the art will appreciate, the fourth layer 40 is connected to the bottom layer 50 in a similar fashion, such that each of the linear microfluidic channels 58 of the bottom layer are in communication with three of the plurality of holes 42 of the fourth layer. In a further aspect, the second and fourth layers 20, 40 are connected to the respective top and bottom layers 10, 50 using the layers of silicon 21, 41 that are deposited on the second and fourth layers, and no longer are exposed externally.

In a further aspect, the third layer 30, which is preferably formed of a hydrophobic substance (e.g., PDMS), has a plurality of holes 32 that extend from the top surface 34 to the bottom surface 36 of the third layer. In one aspect, the plurality of holes 32 in the third layer 30 are configured in a 3×3 array. The array of the third layer is substantially the same as the array formed in the respective second and fourth layers 20, 40, such that, when the third layer 30 is interposed therebetween the second and fourth layers, the plurality of holes 22, 32, 42 in the respective second, third, and fourth layers form a plurality of fluid passageways 11 that are in communication with the linear microfluidic channels of the respective top and bottom layers 10, 50. In one exemplary aspect, when the substrate is formed, the linear microfluidic channels of the top layer can be positioned at an angle, for example a right angle, with respect to the linear microfluidic channels of the bottom layer. FIG. 9 shows an exploded view of the assembled device.

The device shown in FIG. 9 can be assembled as follows: The top and second layers 10, 20 and the fourth and bottom layers 40, 50 can be anodically bonded together. Following activation of the third, hydrophobic PDMS, layer with an oxygen plasma, the bonded top and second layers can be aligned with and then bonded to the activated PDMS layer 30. Then the bonded fourth and bottom layers can be bonded to the similarly activated bottom surface of the third layer 30.

Upon completion of device fabrication, electrodes and fluidic tubing can be connected to the inlet and outlet of each of the three microfluidic channels on the top and bottom of the now monolithic bonded device. Assembled in this way, it can be seen that there is now only a limited region of the device in which the solvent-absorbing hydrophobic substance (PDMS in this example) is exposed to the fluidic flows. This can control the solvent extraction to a very high degree. Also, because the microfludic channels of the top and bottom layers are configured to be positioned substantially perpendicular relative to each other, an individual hole can be addressed electrically and fluidically by activating only one electrode on the top and one electrode on the bottom. There will then be only one unique electrical and fluidic path through the device. Therefore, only one membrane will be manipulated or probed. As one skilled in the art will appreciate, different membranes can be probed by activating different electrode rows and columns. Although the device can allow each membrane to be addressed and probed individually, the device can also be used to manipulate multiple membranes simultaneously by activating an entire fluidic row or column.

This device architecture can also be used to increase the membrane density by decreasing the hole size in selective layers, while minimizing concern about fluidic resistance in the main channels because their size can remain unchanged. Although there will be increased fluidic resistance through the hole as a result of Poiseuille's equation, its effect can be limited by decreasing the thickness of the glass and hydrophobic layers that contain the holes. Achieving high membrane densities can be of significant interest to pharmaceutical companies for high throughput drug safety screening and drug discovery of ion channels, as well as other applications such as ion channel-based sensing.

While the device shown in FIGS. 8 and 9 is for a 3×3 array, many other arrays are contemplated. For example, the device can have a 1×1, 2×2, 3×3, 4×4, 5×5, 6×6, 7×7, 8×8, 9×9, 10×10, 11×11, 12×12, 13×13, 14×14, 15×15, 16×16, 17×17, 18×18, 19×19, 20×20, 21×21, 22×22, 23×23, 24×24, 25×25, 26×26, 27×27, 28×28, 29×2, 30×30, 31×31, 32×32, 33×33, 34×34, 35×35, 36×36, 37×37, 38×38, 39×39, 40×40, 41×41, 42×42, 43×43, 44×44, 45×45, 46×46, 47×47, 48×48, 49×49, 50×50, 51×51, 52×52, 53×53, 54×54, 55×55, 56×56, 57×57, 58×58, 59×59, 60×60, 61×61, 62×62, 63×63, 64×64, 96×96, 128×128, 160×160, 192×192, 224×224, or 256×265 array of microfluidic channels.

Hydrophobic Substance

The disclosed device can be entirely or partially constructed of a hydrophobic substance. For example, the substrate and the microfluidic channels can be constructed of hydrophobic substances or just the microfluidic channels (e.g., the substrate can be constructed of glass with microfluidic channels etched or drilled therein and one or more of the microfluidic channels can be coated with a hydrophobic substance). It is also contemplated that a portion of the microfluidic channels can be comprised of a hydrophobic substance. For example, one or more second microfluidic channels can comprise a hydrophobic substance or both first and second microfluidic channels can comprise a hydrophobic substance.

Any hydrophobic substance can be used in the disclosed devices. For example, the hydrophobic substance can comprise a hydrophobic polymer. Examples of hydrophobic polymers comprise single hydrophobic polymers or mixtures of hydrophobic polymers. Also, either the hydrophobic polymer can be a homopolymer or copolymer (e.g., random copolymers, graph copolymers, block copolymers, and the like). Suitable hydrophobic polymers are readily available from commercial sources and/or can be prepared by methods known to those of ordinary skill in the art. Specific examples of suitable hydrophobic polymers comprise, and are not limited to, polyolefins (e.g., polyethylene, polypropylene, polystyrene, poly(meth)acrylate, polymethyl(meth)acrylate, polydivinylbenzene, fluorinated polydivinylbenzene, poly (N-vinylpyrrolidone, or mixtures thereof), polyesters (e.g., polyethylterephthalate), polyamides (e.g., nylon), $C_8$-$C_{18}$ alkanes immobilized on silica, and mixtures thereof. In one particular example, the hydrophobic substance is PDMS.

Methods of Using the Device

The disclosed devices can be used to form bilayers and membranes. In the disclosed method, the first microfluidic channels can be contacted with an organic solution. The organic solution can comprise one or more lipids and/or amphiphiles, i.e., the compound(s) used to form the bilayer or monolayer membrane. It is contemplated that any compound that forms a bilayer or monolayer membrane can be used. Examples of these are disclosed elsewhere herein. It is further contemplated that a single type of lipid or amphiphiles or mixtures thereof can be used. The organic solution can contain any nonpolar solvent. Examples of suitable nonpolar solvents comprise, and are not limited to, propane, butane, pentane, hexane, heptane, octane, nonane, decane, hexadecane, cyclopentane, cyclohexane, benzene, toluene, squalene, xylene, diethyl ether, diisopropylether, ethylacetate, 2-butanone, carbon tetrachloride, chloroform, methylene chloride, tetrachloroethane, trichlorethane, dichloroethane, ethyl acetate, and the like. In one particular example, the organic solution comprises 1:1 squalene:n-decane.

The organic solution can contain buffers, preservatives, surfactants, stabilizers, proteins or other biomolecules of interest, and the like. In one example, the organic solution comprises a perfluoroalkylene compound (e.g., perfluorooctane).

Also, the one or more second microfluidic channels can be contacted with an aqueous solution. The aqueous solution can contain buffers, surfactants, preservatives, proteins or other biomolecules of interest, and the like. In one specific example, the aqueous solution contains a hydrogel prepolymer, such as those disclosed herein.

The flow of the organic solution (with the lipid) and the aqueous solution through the microfluidic channels can be adjusted so that the organic solution forms a droplet in the aqueous solution. As noted, in the disclosed devices, the at least one first microfluidic channel in connected to and in communication with the at least one second microfluidic channel. Thus, an organic solution flowing through a first microfluidic channel will flow into a second microfluidic channel, through which an aqueous solution is present. By adjusting the flow of the organic and/or aqueous solutions through the first and second microfluidic channels respectively, the organic solution can form a droplet in the aqueous solution.

The movement of the organic and/or aqueous solutions through the microfluidic channels can be controlled in any manner known to one of ordinary skill in the art. For example and without limitation, the solutions can also be moved through the microfluidic channels with syringe pumps, external and internal peristaltic pumps, by applying a vacuum, by applying an electric potential, by allowing a gas to flow over and/or through the microfluidic channels. Also, temperature gradients can move volumes of solutions through the microfluidic channels.

Once the organic solution (containing amphiphilic molecules) forms a droplet between volumes of the aqueous solution, and is thus inside the second microfluidic channel, the droplet can come into contact with the hydrophobic substance of the second microfluidic channel (e.g., PDMS).

Here, the organic solvent can partition into the hydrophobic substance of the second microfluidic device, and the amphiphilic molecules can thereby form a substantially stable bilayer or monolayer membrane. This process is illustrated in FIGS. 1-4.

In a further aspect, the disclosed device can also be integrated with a detection apparatus to monitor the formation, stability, and other characteristics of the bilayer, or various interactions between compounds as disclosed herein. Suitable detection apparatus are known in the art and comprise, for example and without limitation, an optoelectronic detector, UV detector, refractive index detector, fluorescence detector, conductivity detector, electrochemical detector, FTIR detector, thermal conductivity detector, flame ionization detector, photoionization detector, mass spectroscopy detector, calorimetric detector, and other common analytical detectors known to one of ordinary skill in the art. The choice of the detection apparatus can be determined by one of ordinary skill in the art depending on the device, the bilayer or monolayer, any additional components or compounds, the property being measure, and the like.

Method of Encapsulating Bilayer and Monolayer Membranes

In a further aspect, disclosed herein are long-lived and physically robust bilayer and monolayer membranes encapsulated in a polymer hydrogel. Methods for the creation of such encapsulated bilayer and monolayer membranes in situ are also disclosed and contemplated herein. For example, disclosed is a method of encapsulating a bilayer or monolayer membrane comprising forming a bilayer or monolayer membrane and polymerizing a hydrogel prepolymer in the presence of the bilayer or monolayer membrane, thereby forming a hydrogel encapsulated bilayer or membrane. In some examples, the hydrogel prepolymer can be contacted to the bilayer or monolayer membrane after its formation and then polymerized or, alternatively, the hydrogel prepolymer can be present before or during the formation of the bilayer or monolayer membrane and then polymerized.

Bilayer and Monolayer Membrane Formation

The formation of the bilayer or monolayer membrane can be by any method known in the art for forming bilayer or monolayer membranes. For example, the method disclosed in Mueller et al., *Nature* 1962, 194:979-980, which is incorporated by reference herein for at least its teaching of methods to form lipid bilayer membranes, can be used. In another example, the device and method disclosed herein for forming a bilayer or monolayer membrane can be used. In this example, the hydrogel prepolymers can be present initially or subsequently added after bilayer or monolayer membrane formation in the aqueous solution.

In one example, a bilayer or monolayer membrane can be prepared from mixtures of two or more lipids or amphiphiles. Suitable lipids can be generally classified as ionic (anionic/cationic/dipolar) and nonionic. More specifically, polymeric surfactants, silicon surfactants, fluorinated surfactants, oligomeric surfactants, dimeric surfactants, natural lipids, amphiphiles, amphiphilic polymers and the like, are suitable lipids for the devices and methods disclosed herein.

In one example, the bilayer or monolayer membranes disclosed herein can comprise an anionic lipid. Any anionic lipid can be used. Suitable anionic lipids are commonly used in detergents, shampoos, soaps, etc., and can be obtained commercially or prepared by methods known in the art. They comprise, and are not limited to, alkylbenzene sulfonates (detergent), fatty acid based surfactants, lauryl sulfate (e.g., a foaming agent), di-alkyl sulfosuccinate (e.g., a wetting agent), lignosulfonates (e.g., a dispersant), and the like, including mixtures thereof. In other examples, linear alkylbenzene sulphonic acid, sodium lauryl ether sulphate, alpha olefin sulphonates, phosphate esters, sodium sulphosuccinates, hydrotropes, and the like, including mixtures thereof, can be used.

In another aspect, the bilayer or monolayer membranes disclosed herein can comprise a cationic lipid. Any cationic lipid can be used. Suitable cationic lipids comprise, and are not limited to, quaternary ammonium compounds (e.g., tetraalkyl ammonium salts, pyridinium salts, imidazolinium salts, and the like). Such cationic lipids can be obtained commercially or can be prepared by methods known in the art.

In still another aspect, the bilayer or monolayer membranes disclosed herein can comprise a nonionic lipid. Any nonionic lipid can be used. Suitable nonionic lipids do not ionize in aqueous solution, because their hydrophilic group is of a non-dissociable type, such as alcohol, phenol, ether, ester, or amide. They can be classified as ethers (e.g., polyhydric alcohols such as glycerin, solbitole, sucrose, etc.), fatty acid esters (e.g., glycerin fatty acid ester, sobitan fatty acid ester, sucrose fatty acid ester, etc.), esters (e.g., compounds made by applying, for example, ethylene oxide to a material having hydroxyl radicals such as high alcohol, alkyl-phenol, and the like), ether/esters (e.g., compounds made by applying, for example, the ethylene oxide to the fatty acid or polyhydric alcohol fatty acid ester, having both ester bond and ether bond in the molecule), and other types (e.g., the fatty acid alkanolamide type or the alkylpolyglyceride type). Other suitable examples of nonionic lipids can comprise, and are not limited to, alcohol ethoxylates and alkyl phenol ethyoxylates, fatty amine oxides, alkanolamides, ethylene oxide/propylene oxide block copolymers, alkyl amine ethoxylates, tigercol lubricants, etc.

In yet another aspect, the bilayer or monolayer membranes disclosed herein can comprise dipolar lipids. Any dipolar lipid can be used. Suitable dipolar lipids (called amphoteric or zwitterionic) exhibit both anionic and cationic dissociation. Suitable examples of dipolar lipids comprise, and are not limited to, products like betaines or sulfobetaines and natural substances such as amino acids and phospholipids. In one aspect, the betaines disclosed in U.S. Pat. Nos. 6,852,816; 6,846,795; 6,846,352; and 6,849,426, which are incorporated by reference in their entireties, can be used herein.

In still another aspect, the bilayer or monolayer membranes disclosed herein can comprise additional membrane forming amphiphilic molecules. Any amphiphilic molecule can be used, examples of which comprise multiblock copolymers. Suitable examples of block copolymers comprise, and are not limited to, products like poly(methyl oxazoline)-poly(dimethyl siloxane)-poly(methyl oxazoline), poly(ethylene glycol)-poly(dimethyl siloxane)-poly(ethylene glycol), poly (ethylene oxide)-polybutadiene, poly(ethylene oxide)-polystyrene, poly(acrylic acid)-polystyrene, polyisoprene-poly(2-cinnamoylethyl methacrylate), polystyrene-(isocyano-L-alanine-L-alanine), poly(ethylene oxide)-poly (ethylene ethylene), poly(acrylic acid)-poly(methyl methacrylate), poly(methacrylic acid)-poly(neopentyl methacrylate), poly(t-butylmethacrylate)-poly(ethylene oxide), poly(methyl methacrylate)-poly(N,N-dimethylacrylamide), poly(butylacrylate)-poly(acrylic acid), poly(butadiene)-poly (methacrylic acid), poly(butadiene)-poly(acrylic acid), poly (isoprene)-poly(ethylene oxide), poly(ethylene)-poly(ethylene oxide), poly(ethylene-co-butene)-poly(ethylene oxide), poly(ethylene oxide)-poly(acrylic acid), poly(ethylene oxide)-poly(eta-caprolactone), poly(ethylene oxide)-poly (methyl methacrylate), poly(ethylene oxide)-poly(2-hydroxyethyl methacrylate), poly(ethylene oxide)-poly(methacrylic acid), poly(ethylene oxide)-poly(2-methyl oxazoline), poly(ethylene oxide)-poly(propylene oxide), poly(ethylene oxide)-poly(t-butyl acrylate), poly(ethylene oxide)-poly(tetrahydrofurfuryl methacrylate), poly(ethylene oxide)-poly(acrylic acid), poly(ethylene oxide)-poly(methyl acrylate), poly(ethylene oxide)-poly(t-butyl methacrylate), poly(ethylene oxide)-poly(2-ethyl oxazoline), poly(isobutylene)-poly(ethylene oxide), polystyrene-poly(acrylic acid), polystyrene-polyacrylamide, poly(p-chloromethyl styrene)-polyacrylamide, poly(styrene-co-p-chloromethyl styrene)-poly(acrylic acid), polystyrene-poly(methacrylic acid), polysytrene-poly(N,N-dimethylacrylamide), poly(dimethylsiloxane)-poly(acrylic acid), poly(dimethylsiloxane)-poly(ethylene oxide), poly(2-vinyl naphthalene)-poly(acrylic acid), poly(2-vinyl pyridine)-poly(ethylene oxide), poly(N-methyl 2-vinyl pyridine)-poly(ethylene oxide), poly(vinyl pyrrolidone)-(D/L-lactide), poly(dimethylsiloxane)-block-poly(2-methyloxazoline) (PMOXA-PDMS-PMOXA), poly(ethylene oxide)-polypropylene oxide) (EO-PO-EO) poly(acrylic acid)-poly(9,9-di-n-hexyl-2,70fluorene)-poly(acrylic acid), poly(n-butyl acrylate)-poly(9,9-di-n-hexyl-2,70fluorene)-poly(n-butyl acrylate), poly(t-butyl acrylate)-poly(9,9-di-n-hexyl-2,70fluorene)-poly(t-butyl acrylate), poly(t or n-butyl acrylate)-poly(methyl methacrylate)-poly(t or n-butyl acrylate), poly(t-butyl acrylate)-polystyrene-poly(t-butyl acrylate), poly(ethylene oxide)-poly(dimethylsiloxane)-poly(ethylene oxide), poly(ethylene oxide)-polystyrene-poly(ethylene oxide); poly(ethylene oxide)-poly(methylphenylsilane) pentablock: (PMPS-PEO)2-PMS; all combinations of the blocks listed are also possible.

Other examples of suitable lipids include natural surfactants, which can have their source from plant or animal organs. In another example, a bolaform amphiphile can be used. A bolaform amphiphile is a compound that has two hydrophilic head groups at opposite ends of a hydrophobic tail.

Mixtures of these lipids and amphiphiles can also be used in the compositions and methods disclosed herein.

In one specific example, the disclosed bilayer comprises diphytanoylphosphatidylcholine.

Hydrogel Prepolymer

In the disclosed methods, any hydrogel prepolymer can be used. A hydrogel prepolymer is any monomer or oligomer that can be polymerized to provide a hydrogel. Hydrogels are three-dimensional polymer networks composed of homopolymers or copolymers that are capable of absorbing large amounts of water. Thus, a characteristic of hydrogels is that they swell in water or aqueous fluids without dissolving. Their high water content and soft consistency make hydrogels similar to natural living tissue more than any other class of synthetic biomaterials. Accordingly, many hydrogels are compatible with living systems and hydrogels have found numerous applications in medical and pharmaceutical industries. In the disclosed methods, polymerizing the hydrogel prepolymer in the presence of a bilayer or monolayer membrane can result in a hydrogel that encapsulates and thus stabilizes the bilayer.

Suitable prepolymers can be obtained commercially or prepared by methods known in the art. Examples of suitable hydrogel prepolymers that can be used in the disclosed methods comprise, and are not limited to, any number of prepolymers based on diol- or glycol-containing linkages, for example, prepolymers comprising polyethylene glycol (PEG), also known as polyethylene oxide (PEO), and polypropylene oxide (PPO). Other suitable examples comprise prepolymers comprising polyester, which can be polymerized with prepolymers comprising PEG to form a hydrogel with multiple segments or blocks of PEG alternating with blocks of polyester. Other examples of prepolymers comprise hydroxyalkanoates, propylene fumarate, vinylpyrrolidone, vinyl polypyrrolidone, vinyl N-methylpyrrolidone, hydroxypropylcellulose, methylcellulose, sodium alginate, gelatin, acid-hydrolytically-degraded gelatin, agarose, carboxymethylcellulose, carboxypolymethylene, hydroxypropyl methacrylate, hydroxyethyl methacrylate, acrylic acid, acrylamide, N-isopropylacrylamide, N,N-dimethylacrylamide, hyaluronic acid, collagen, and 2-hydroxypropyl methacrylamide. One specific example comprises polyethylene glycol-dimethacrylate (PEG-DMA) monomers.

In other examples, the prepolymers can be any prepolymer that results in one of the following hydrogels: aminodextran, dextran, DEAE-dextran, chondroitin sulfate, dermatan, heparan, heparin, chitosan, polyethyleneimine, polylysine, dermatan sulfate, heparan sulfate, alginic acid, pectin, carboxymethylcellulose, hyaluronic acid, agarose, carrageenan, starch, polyvinyl alcohol, cellulose, polyacrylic acid, carboxymethyl dextran, polyacrylamide, polyethylene glycol, poly(N-isopropyl acrylamide), poly(hydroxy ethylmethacrylate), polyethylene glycol diacrylate, polyethylene glycol dimethacrylate, and combinations thereof.

Polymerization of the prepolymers can be performed by methods known in the art and will depend on the particular prepolymer, the presence of crosslinkers, the type of bilayer, the presence of additional components, preference and the like. In some examples, polymerization can be thermally initiated, and thus performed by heating the prepolymers, or polymerization can be chemically initiated, and thus performed by adding a chemical initiator to the prepolymers. In other examples, the polymerization can be photoinitiated, and thus performed by exposing the prepolymers to radiation (e.g., UV radiation with or without a photoinitiator, depending on the prepolymer).

Encapsulated Bilayer and Monolayer Membranes

Disclosed herein are hydrogel encapsulated bilayer and monolayer membranes, i.e., hydrogel encapsulated membranes (HEMs). The HEMs can be prepared by the methods disclosed herein. The disclosed HEMs can comprise any bilayer or monolayer membrane, for example, a bilayer or monolayer comprising any of the lipids and/or amphiphiles disclosed herein. In other examples, the disclosed HEMs can comprise any hydrogel, for example, any hydrogel disclosed herein or any hydrogel prepared from any of the hydrogel prepolymers disclosed herein.

Additional Components

The HEMs disclosed herein can also comprise additional components. For example, additional components can be added to make the membrane more stable. Suitable additional components can comprise, and are not limited to, preservatives, antioxidants, stabilizers, and the like. Other components that can be present in the disclosed HEMs are biomolecules and other molecules of interests. For example, membrane-associated proteins can be present in the disclosed HEMs. Other additional components comprise, and are not limited to, the "first compounds" and "second compounds" disclosed herein below.

Methods of Using HEMs

The HEMs disclosed herein can be used for many varied uses. Hydrogel encapsulation of bilayer or monolayer membranes can impart durability, mechanical stability, and longevity necessary for extended single-molecule biophysical studies of integral membrane proteins and engineered device applications of these proteins. The hydrogels can further allow the membrane access to a bulk-like aqueous environment, enabling a low resistance path to the pore for ionic currents and diffusing analytes.

In some example, the disclosed HEMs can be used for field applications of protein-based sensors and investigations of interactions between membrane proteins and small molecules for drug discovery. Of particular interest is the potential of the gel to slow the transit of single stranded DNA driven electrophoretically through the pore for the purposes of electrical characterization.

In some other examples, the disclosed HEMs can be used for chemical and biochemical synthesis, chemical and biological assays, as a biochemical sensor, drug delivery, purification in biology, to measure various properties, conditions, and/or interactions, and the like.

In one example, disclosed herein are methods of assaying an interaction between a first compound and a second compound, comprising providing a HEMs as disclosed herein, wherein the HEMs comprises the second compound; contacting the HEMs with the first compound; and detecting an interaction between the first compound and the second compound. A detectable interaction can indicate that the first compound has an activity or specific affinity for the second compound or vise-versa.

Interaction

The term "interaction" means and is meant to include any measurable physical, chemical, or biological affinity between two or more molecules or between two or more moieties on the same or different molecules. As will be understood from the compositions and methods disclosed herein, any measurable interaction between molecules can be involved in and are suitable for the methods and compositions disclosed herein. General examples include interactions between small molecules, between proteins, between nucleic acids, between small molecules and proteins, between small molecules and nucleic acids, between proteins and nucleic acids, and the like.

An interaction can be characterized by a dissociation constant of at least about $1 \times 10^{-6}$ M, generally at least about $1 \times 10^{-7}$ M, usually at least about $1 \times 10^{-8}$ M, or at least about $1 \times 10^{-9}$ M or $1 \times 10^{-10}$ M or greater. An interaction generally is stable under physiological conditions, including, for example, conditions that occur in a living individual such as a human or other vertebrate or invertebrate, as well as conditions that occur in a cell culture such as used for maintaining mammalian cells or cells from another vertebrate organism or an invertebrate organism.

Examples of interactions that can be involved in and/or determined by the compositions and methods disclosed herein comprise, and are not limited to, an attraction, affinity, a binding specificity, an electrostatic interaction, a van der Waals interaction, a hydrogen bonding interaction, and the like.

One specific type of interaction that can be involved in and/or determined by the methods and compositions disclosed herein is an interaction between a ligand (e.g., a potential therapeutic agent, a small molecule, an agonist, an antagonist, an inhibitor, an activator, a suppressor, a stimulator, and the like) and a protein (e.g., a receptor, a channel, a signal transducer, an enzyme, and the like). For example, an interaction between a potential therapeutic agent and a target protein can indicate a potential therapeutic activity for the agent. In another example, an interaction between a small molecule (e.g., a lipid, a carbohydrate, etc.) and an enzyme (e.g., a kinase, a phosphatase, a reductase, an oxidase, and the like) can indicate enzymatic activity or substrate specificity.

In another example of a type of interaction that can be involved in and/or determined by the methods and compositions disclosed herein is an interaction between two proteins or fragments thereof (e.g., an enzyme and a protein substrate or an antibody and an antigen or an epitope of an antigen). An example of this interaction can comprise, but is not limited to, the binding of a kinase, a protease, a phosphatase, and the like to a substrate protein. Such interactions can, but need not, result in a reaction or chemical transformation (e.g., phosphorylation, cleavage, or dephosphorylation). Another example of an interaction includes the binding or affinity of an antibody for an antigen or epitope of an antigen.

Another type of interaction that can be involved in and/or determined by the methods and compositions disclosed herein is hybridization between two nucleic acid sequences (e.g., a prime, probe, aptamer, ribozyme, and the like hybridizing to a target sequence of a nucleic acid). The term "hybridization" typically means a sequence driven interaction between at least two nucleic acid molecules, such as a primer or a probe and a gene. "Sequence driven interaction" means an interaction that occurs between two nucleotides or nucleotide analogs or nucleotide substitute in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Another type of interaction that can be involved in and/or determined by the compositions and methods disclosed herein includes a Watson-Crick interaction, i.e., at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is another example and is the interaction that takes place on the Hoogsteen face of a nucleotide or nucleotide analog, which is exposed in the major groove of duplex DNA. The Hoogsteen face includes the N7 position and reactive groups ($NH_2$ or O) at the C6 position of purine nucleotides.

Yet another type of interaction that can be involved in and/or detected by the compositions and methods disclosed herein includes an interaction between a protein (e.g., a polymerase, endonuclease, or ligase) and a nucleic acid.

Detection

Detecting an interaction in the methods disclosed herein can be performed by any method, but will usually depend on the particular interaction being detected. For example, the first compound and/or second compound may contain a fluorescent marker, and detection of an interaction can be made by measuring fluorescence or changes in fluorescence. In another aspect, detecting an interaction can involve identifying a particular product. For example, if the first and second compound interact in such a way as to produce a reaction product (e.g., a kinase phosphorylating a substrate protein, a protease cleaving a particular protein, an endonuclease cleaving a particular nucleic acid, a ligase ligating nucleic acids, and the like), detection can be accomplished by identifying a particular product (e.g., the phosphorylated or cleaved product). Identifying a product can be done by known methods such as chromatography (e.g., retention times or $R_f$), fluorescence detection, ionization, mass spectral analysis, nuclear magnetic resonance imaging, immunohistological techniques, microscopy (e.g., TEM, SEM, optical microscope, or AFM), XRD, XPS, AES, infrared spectroscopy, electrochemical analysis (e.g., cyclic voltametry or impedance spectroscopy), dynamic light scattering, and the like. In a particular example, detection can comprise the measurement of electrical properties, e.g., the conductivity, resistance, capacitance of the bilayer in the HEMs.

First and Second Compounds

In the disclosed methods the first compound can be any molecule that one may desire to measures a potential interaction with any other desired molecule. For example, the first compound can be any of the additional components disclosed herein, for example, amino acid based molecules (e.g., peptide, proteins, enzymes, or antibodies, including variants, derivatives, and analogs thereof), nucleic acid based molecules (e.g., primers, probes, aptamers, or ribozymes, including variants, derivatives, and analogs thereof), small molecules (e.g., biomolecules, drugs, potential therapeutics, or organic and inorganic compounds), other biological molecules, polymers, carbohydrates, lipids, organometallic complexes, and catalysts.

The second compound, which is present in the secondary component, can also be any molecule as described above for the first compound. It is contemplated that the disclosed methods are not limited by the particular order, identity or priority of the first or second component; the identifiers "first" and "second" are merely arbitrary and are used herein to simply distinguish one compound from the other; no connotation of order of addition is intended as any order of the compounds is contemplated and can be used in the methods disclosed herein.

Exemplary Assays

In one example, the second compound can be a protein and the first compound can be a small molecule such as a potential therapeutic agent, a kinase, a phosphatase, a protease, a methylating agent, an antibody, or fragments thereof. Alternatively, the second compound can be a small molecule, a kinase, a protease, a methylating agent, an antibody, or fragment thereof and the first compound can be a target protein. When the second compound is a protein and the first compound is a potential therapeutic or vise-versa, the detectable interaction can indicate a potential therapeutic activity. In this example, the method can be used to screen for potential drugs against a particular protein.

When the second compound is a protein and the first compound is a kinase, a phosphatase, a protease, a methylating agent, or a fragment thereof, or vise-versa, the detectable interaction can indicate enzymatic activity. Thus, in this example, one can analyze the ability of a protease to cleave a particular protein, or the ability of a kinase to phosphorylate a particular protein, or the ability of a protein to be dephosphorylated by a particular phosphatase, and the like.

In another example, the second compound can be a protein, antigen, or epitope, and the first compound can be an antibody or fragment thereof, or vise-versa. Here, the method can be used to detect an interaction that indicates binding activity. Thus, one can use this method to screen antibodies to find those that bind to a particular antigen or epitope. Conversely, one can use the disclosed method to find particular antigens or epitopes recognized by a particular antibody. It can also be possible, when the first compound is a cell or microbe and the second compound is an antibody or fragment thereof, to screen for particular surface antigens on the cell surface, or to screen for antibodies that recognize a given organism. These and other uses are contemplated herein.

In another example, the second compound can be a nucleic acid and the first compound can be a primer, a probe, a ligase, an endonuclease, a transcriptase, a ribozyme, or fragment thereof, or vise-versa, that is the second compound can be a primer, a probe, a ligase, an endonuclease, a transcriptase, a ribozyme, or fragment thereof and the first compound can be a target nucleic acid. When the second compound is a nucleic acid and the first compound is a ligase, an endonuclease, a transcriptase, a ribozyme, or a fragment thereof, or viseversa, the interaction can indicate enzymatic activity. For example, one can use the disclosed method to analyze the ability of an endonuclease to recognize and/or cleave a particular nucleic acid sequence, or the ability of a particular nucleic acid (e.g., a primer) to initiate transcription with a particular transcriptase.

When the second compound is a nucleic acid and the first compound is a primer, probe, or aptamer, or vise-versa, the interaction can indicate hybridization. In this example, one can use the disclosed methods to analyze the ability of a primer or probe sequence to hybridize to a particular nucleic acid sequence.

In the methods disclosed herein, the methods can further comprise contacting the HEMs with a third compound. This can be done to, for example, evaluate or analyze a particular interaction between a first compound and a second compound while a third compound is present. Also, it is contemplated that the methods disclosed herein can further comprise contacting the HEMs with a fourth, fifth, six, etc. compound. Any number of additional compounds can be used in the methods and compositions disclosed herein.

In the methods disclosed herein, the third compound can be any molecule or group of molecules. For example, any of the molecules disclosed herein, such as amino acid based molecules, nucleic acid based molecules, small molecules, macromolecules, cells, etc. Specific examples of suitable third compounds comprise, and are not limited to, an antagonist, an agonist, a ligand, an inhibitor, an activator, a primer, a promoter, a transcription factor, an endonuclease, a ligase, a transcriptase, a protease, a kinase, a phosphatase, a methylating agent, or mixtures thereof.

Nucleic Acid Sequencing

In one specific example, the disclosed HEMs can be used to sequence nucleic acids (e.g., DNA and RNA, including mutants, fragments, and variants thereof). For example, the method can comprise contacting a HEM comprising a channel protein with a nucleic acid and measuring the changes in electronic potential as the nucleic acid passes through the channel protein, wherein a change in electric potential or current correlates to a base or base pair.

Suitable channel proteins are available commercially or can be extracted and purified from any living cells and can be prepared by methods known in the art. Examples of channel proteins that can be used in the disclosed methods comprise, and are not limited to, $\alpha$-hemolysin ($\alpha$HL), OmpF, OmpG, OmpA, any protein with a $\beta$-barrel structure, channel proteins such as Na channels, K channels, Cl channels, ligand gated receptors such as Ach receptors, and channel protein having an $\alpha$-helical structure; in short, any channel through which an ionic current can pass.

EXAMPLES

The following examples are put forth so as to provide those of ordinary skill in the art with a complete disclosure and description of how the compounds, compositions, articles, devices, and/or methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of conditions, e.g., component concentrations, desired solvents, solvent mixtures, temperatures, pressures and other reaction ranges and conditions that can be used to optimize the methods described herein. Only reasonable and routine experimentation will be required to optimize such process conditions.

Example 1

Figure 2:
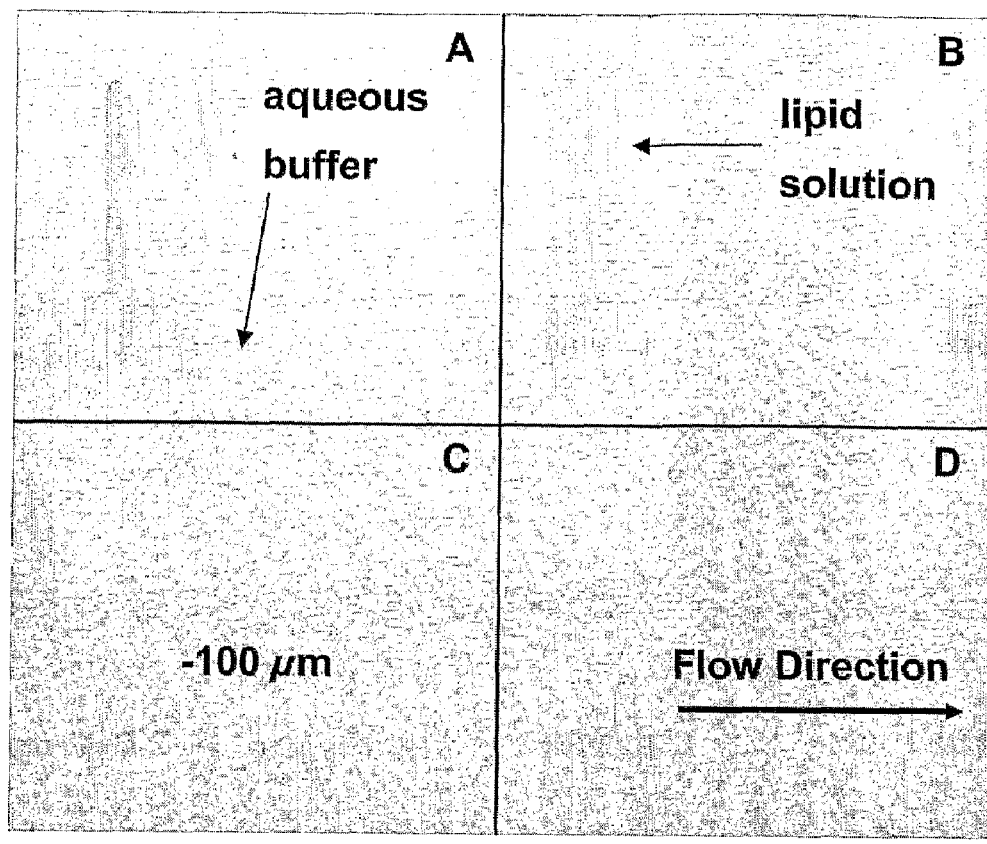
FIG. 2 is a group of micrographs showing the formation of a biphasic aqueous/organic flow in a microfluidic channel. An organic lipid or amphiphile solution is injected into and contained within an aqueous stream (panel B); the aqueous stream then transports the organic droplet elsewhere in the device for further processing. The aqueous stream is colored with food coloring to aid in visual clarity.

Fabrication of Microfluidic Devices from PDMS Using Photolithography and Polymer Molding Disclosed is a biphasic flow formation/solvent extraction microfluidic device. Devices were constructed entirely from PDMS, using standard polymer molding techniques. A microfabrication facility was used in which master molds were fabricated from photoresist on silicon wafers. As shown in FIG. 2, this device comprised two input channels, one each for organic and aqueous solutions, meeting at a junction. Flow driven with precision syringe pumps was sufficient for generating the desired flows; valving was accomplished manually on-device using the technique of Unger et al. (*Science* 2000, 288(5463): 113-116).

Channels were fabricated with dimensions of 100 μm wide×100 μm high×20 mm long. The channel cross-sectional size, 100 μm×35 μm, is similar to that of orifices on which BLMs are formed conventionally. It is contemplated that channel dimensions can be altered to optimize membrane formation: soft lithography techniques allow for the rapid design and fabrication of devices, allowing one to easily examine a variety of channel dimensions. Light microscopy, using a colored dye in the aqueous phase, was used to distinguish it from the lipid solution.

Example 2

Formation of a Biphasic Microfluidic Flow Using Drops of Lipid Solution in an Aqueous Carrier Stream Lipid solutions were prepared in chloroform, a nonpolar solvent immiscible in water having a strong tendency to partition into PDMS (Lee et al., *Anal Chem* 2003, 75(23):6544-6554). A solution containing 0.025 wt % of the lipid diphytonoylphosphatidylcholine (DPhPC) in a solvent system of 1:1 squalene:n-decane with 50 ppm perfluorooctane was used. The biphasic flow configuration shown in FIG. 2 was obtained by controlling two input streams, one comprising of an organic lipid solution, the other containing aqueous buffer (dyed red, containing 1M KCl and 50 mM Hepes buffer at pH 7.5). Both input streams were driven with computer-controlled syringe pumps. These input streams are labeled in FIG. 2A-B, and they meet at a junction to combine in a single output stream.

In FIG. 2A (Lee et al., *Anal Chem* 2003, 75(23):6544-6554), the aqueous input stream is being driven to the output, while the organic stream is allowed to remain stationary. In FIG. 2B, flow is initiated in the organic input stream. Since the two fluids are immiscible, the organic lipid solution forms a droplet in the aqueous stream. In FIG. 2C, this droplet has filled the full width of the output channel. Finally, in FIG. 2D, the flow from the organic input stream has been shut off, allowing this channel to flood with aqueous buffer and pinch off the droplet of lipid solution.

Figure 3:
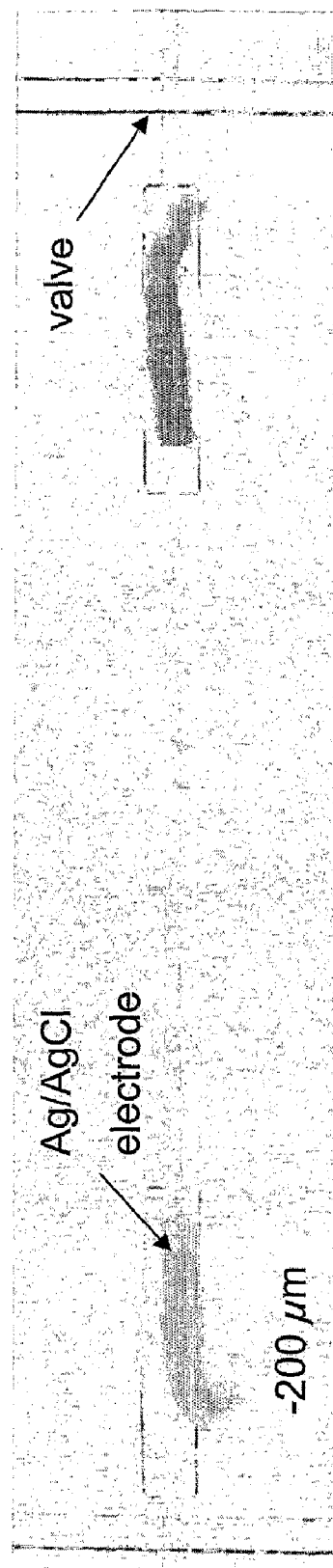
FIG. 3 is a micrograph showing the solvent extraction region of the device can be isolated by pneumatic valves on either side. This region is flanked by Ag/AgCl electrodes that allow for electrical measurements across the membrane as it forms. These electrodes can reside in the same channel as the extraction region as shown, or can reside in connected flanking channels that are not collinear with the main horizontal channel.

FIG. 3 is a micrograph of the region of the device in which solvent extraction takes place. This region has valves on either side that allow for isolation of the droplet as solvent is extracted from it and Ag/AgCl electrodes for measuring the electrical properties of the membrane that is formed by solvent extraction.

Example 3

Figure 4:
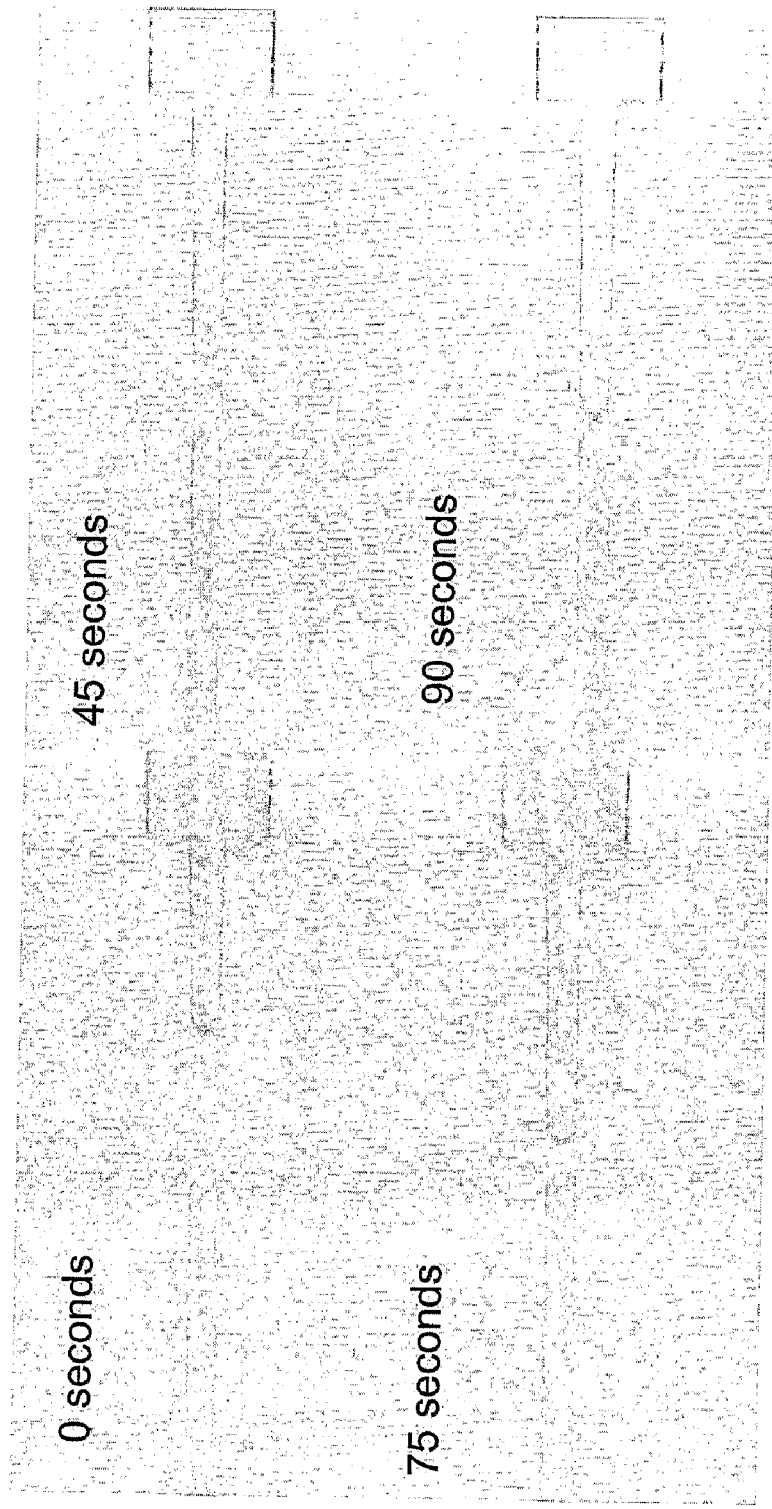
FIG. 4 is a group of time-course micrographs showing solvent extraction from an exemplary lipid solution droplet in an aqueous flow stream. The droplet at 0 seconds was formed by the biphase flow formation method described herein and shown in FIG. 2. Here, flow through the organic input stream was cut off entirely while the pump driving the aqueous input stream was slowed drastically. This driving force was sufficient to push the chloroform in the organic phase entirely into the PDMS. The aqueous stream is colored with food coloring to aid in visual clarity.

Extraction of Organic Solvent from the Lipid Solution Phase to Enable Bilayer Membrane Self-Assembly The extraction of solvent from the organic, lipid-bearing phase was observed. FIG. 4 is a time-course of micrographs showing such an extraction process. This experiment followed the creation of a biphasic flow system, as described above. The valves surrounding the extraction region were closed, and the solvent in the droplet partitioned into the PDMS from which the device was constructed, leaving behind lipid.

Figure 5:
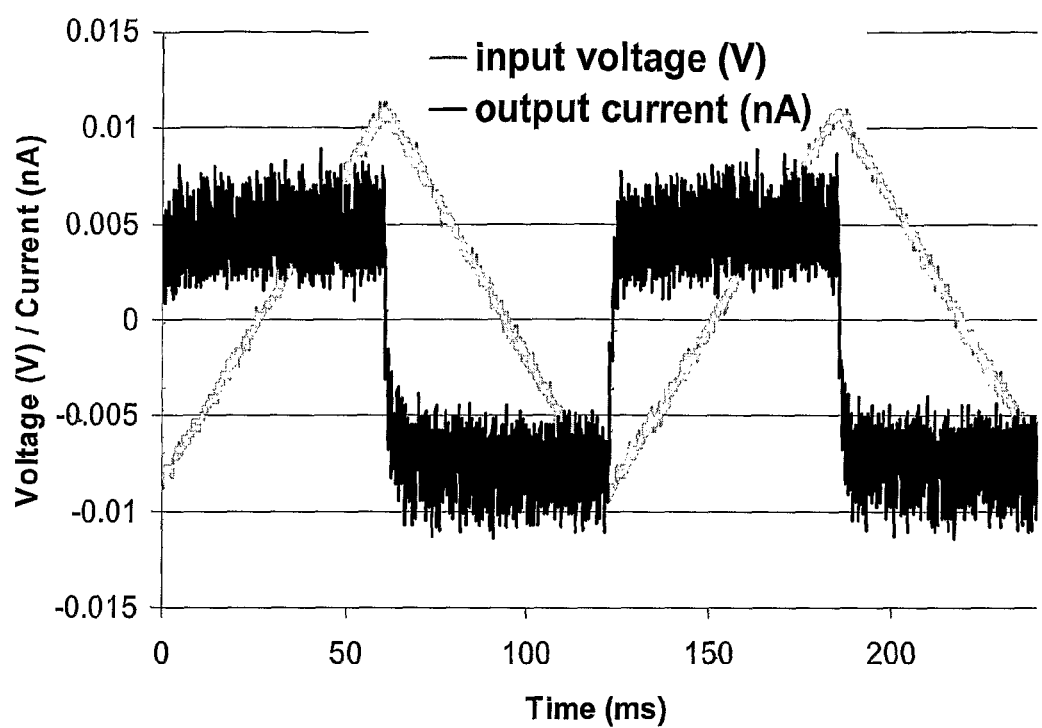
FIG. 5 is a graph of a square-wave current signal (black trace) observed when a triangle-wave voltage (grey trace) is applied between Ag/AgCl electrodes in a microfluidic channel during the process of solvent extraction from a lipid solution droplet, as shown in FIG. 4. The relationship of the current and voltage signals is indicative of a capacitive element within the channel. The amplitude of the square wave allows for a capacitance determination, which reveals the presence of a bilayer membrane and measures its properties.

Electrical observations revealed that these left-behind lipid molecules do, in fact, self-assemble into a bilayer membrane. This conclusion was drawn from measurements of the capacitance across the solvent extraction region of the device. FIG. 5 shows the current measured across a channel in response to an applied triangle-wave potential during such an extraction process. This current takes the form of a square wave, indicating the presence of a capacitive element in the channel. Bilayer membranes are capacitive elements, with the capacitance related to the thickness of the membrane by the equation $C=k\epsilon_0 A/d$, where C is capacitance, k is the dielectric constant of the lipid, $\epsilon_0$ is the permittivity of free space, A is the area of the membrane, and d is the thickness of the membrane. Since the area is equal to the cross-sectional area of the channel, which is known, membrane thickness can be determined from capacitance measurements. Over several experiments, a membrane thickness of 4.8±0.6 nm was measured, as expected for a true molecular bilayer of DPhPC. In addition, the resistance of membranes formed in this manner was measured. All membranes had resistances in the range of 50-100 GΩ, which is more than sufficient for taking single-molecule membrane protein data.

Example 4

Hydrogel-Encapsulated Lipid Membranes

A hydrogel-encapsulated membrane (HEMs) was created by first forming high resistance (>1 GΩ) bilayer membranes on 200 μm-diameter Teflon apertures from a solution of 3 wt % diphytanoylphosphatidylcholine (DPhPC) in n-decane using standard methods (Mueller et al., *Nature* 1962, 194: 979-980). The aqueous solution surrounding these membranes contained 1M KCl, 5 mM HEPES (pH 7.0), 7.5 wt % PEG-DMA monomers (1 kDa, Polysciences, Warrington, Pa.), and 1 wt % Irgacure 2529 UV photoinitiator (CIBA Specialty Chemicals, Tarrytown, N.Y.). Following membrane formation, PEG-DMA polymerization was triggered by exposure to broad spectrum UV light for 5-6 minutes. The membranes before and after gelation were probed electrically using Ag/AgCl electrodes connected to an Axopatch 200B amplifier (Axon Instrument, Foster City, Calif.). Of the 50 runs performed, the formed HEMs remained intact for a mean duration of 48 hours, with some lasting up to 5 days, as compared to a mean duration of 12 hours (with a maximum of about 24 hours) without the presence of the gel.

The electrical characteristics of HEMs were consistently stable over this period of time. Membrane thickness was determined by measuring the capacitance of the bilayer (Alvarez et al., Ion Channel Reconstitution. ed. Plenum Press: New York, 1986; pp. 115-139). The approximate thickness of the HEM was calculated to be 4.7 nm (n=25), consistent with a molecular bilayer of DPhPC. HEM resistance was consistently greater than 10 GΩ over the period the membranes remained intact. In addition, HEMs showed unusual mechanical stability. While planar lipid membranes are typically quite susceptible to mechanical and acoustic perturbation, chambers containing HEMs could be handled roughly with no ill effect to the membrane.

Using the method of Canal and Peppas (*J Biomed Mater Res* 1989, 23(10):1183-1193), the hydrogel polymer mesh size was determined to be about 7 nm. To establish that this gel allows the diffusion of molecules of interest to the encapsulated membrane, the pore protein α-hemolysin (αHL) was introduced to the HEM. αHL is a 34 kD water-soluble polypeptide that combines with other αHL monomers to form a mushroom-shaped heptameric pore in lipid membranes (Song et al., *Science* 1996, 274(5294):1859-66). 1.7 ng of heptameric αHL in an aqueous solution of 200 mM NaCl, 100 mM Tris HCl was deposited atop the gel. αHL insertion into the membrane was observed as a discrete 0.79 nS jump in membrane conductance within 2-10 hours of this deposition. Without the presence of the gel, addition of the same amount of protein resulted in the first incorporation about 0.5-2 hours later in an unstirred solution. The increase in time is consistent with a 3.3-fold increase of the effective diffusion constant of the protein caused by the gel, as predicted by the theory of Lustig and Peppas (*J Appl Polymer Sci* 1988, 36(4):735-747) for the gel mesh size and protein molecular weight in question.

Figure 6:
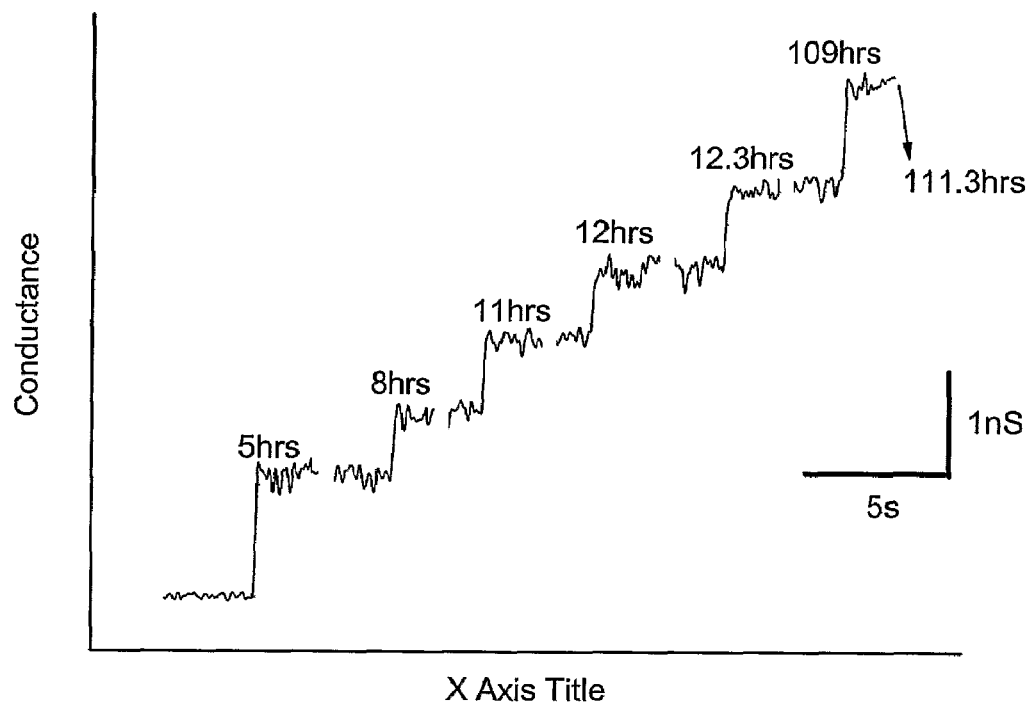
FIG. 6 is a graph of stable single channel currents of the channel protein α-hemolysin (αHL) in a hydrogel encapsulated membrane measured for several days.

Hydrogel encapsulation greatly stabilized the membranes and protein incorporated into them. Stable single channel currents of α-hemolysin in a HEM were measured for several days (FIG. 6). The voltage gating property and characteristic conductance of αHL in DPhPC were measured. Upon application of a 100 mV potential, spontaneous closure of active αHL was observed, a well-known characteristic of α-toxin pores (Bainbridge et al., *FEBS Lett* 1998, 431(3):305-308).

Example 5

Nucleotide Sequencing with Hydrogel-Encapsulated Membranes

Figure 7:
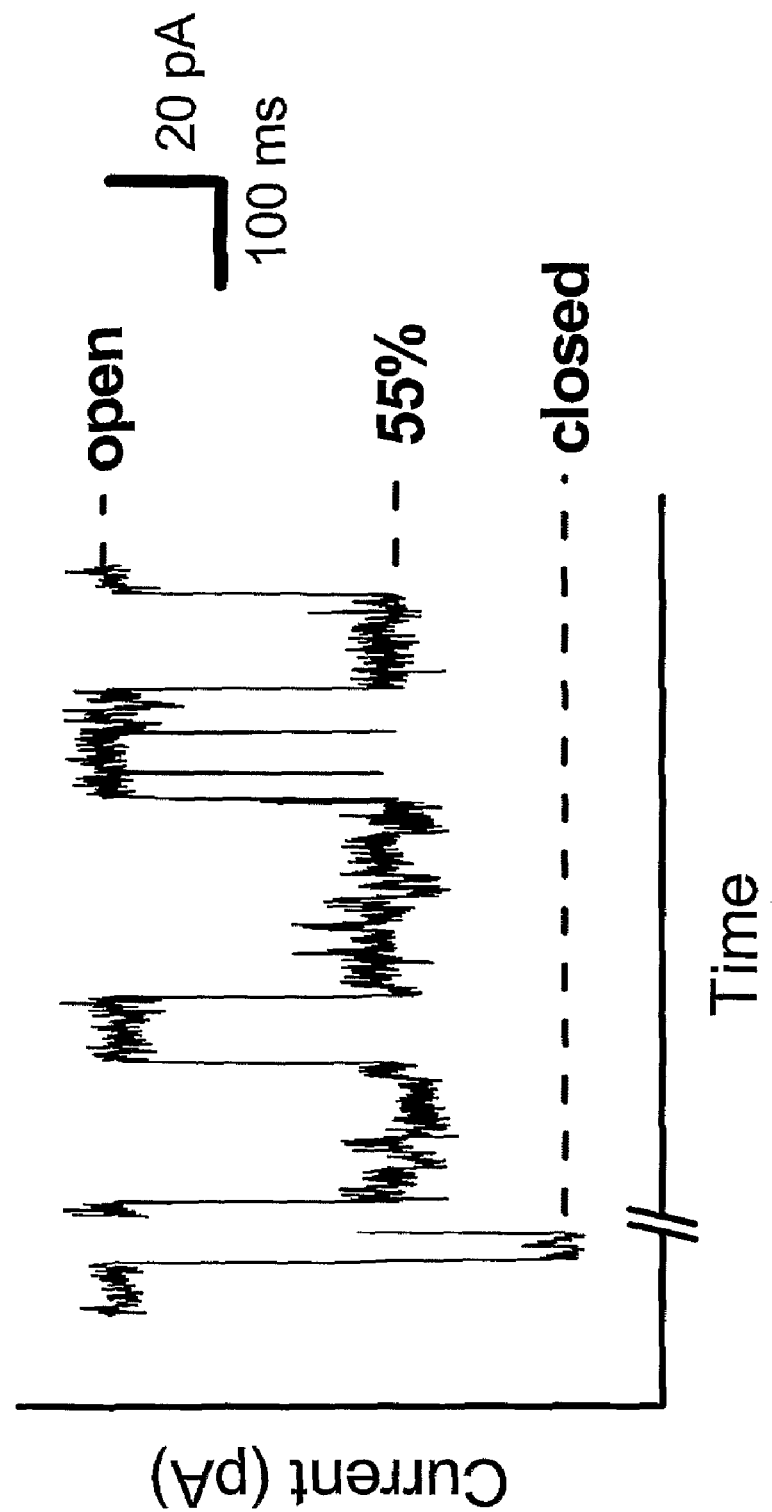
FIG. 7 is a trace of DNA translocation through αHL incorporated into a hydrogel encapsulated membrane in an 80 mV potential. Three blockages of 55% of the open channel current are seen of duration 125, 180, and 86 ms.

To demonstrate the delivery of analyte molecules to a channel protein embedded in a HEM, 150 base-long single strands of poly(AxCy) DNA were added to HEMs containing incorporated αHL. Recent work examining the electrophoretic transport of DNA through nanopores has observed that the DNA travels through the pore so quickly that the passage of single bases cannot be resolved at standard electronic measurement bandwidths (Kasianowicz et al., *Proc Natl Acad Sci USA* 1996, 93:13770-13773; Meller et al., *Proc Natl Acad Sci USA* 2000, 97:1079-1084; Akeson et al., *Biophys J* 1999, 77:3227-3233). In the devices, methods, and compositions disclosed herein, 40 minutes after the addition of DNA, current blockages were observed 3-700 msec in length, about 100× longer than those reported previously (FIG. 7). This DNA is not expected to have any secondary structure, so the delayed transit time is presumed due solely to the additional drag on the translocating oligonucleotide by the presence of the gel. The slowest translocation times indicate that each base requires about ms to traverse the pore, well within the reach of conventional electronics.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

Akeson, M.; Branton, D.; Kasianowicz, J.; Brandin, E.; Deamer, D. W., Microsecond Time-Scale Discrimination Among Polycytidylic Acid, Polyadenylic Acid, and Polyuridylic Acid as Homopolymers or as Segments Within Single RNA Molecules. *Biophys J* 1999, 77:3227-3233.

Alvarez, O., How to set up a bilayer system. In Ion Channel Reconstitution, ed.; Miller, C., Ed. Plenum Press: New York, 1986; pp. 115-139.

Anrather, D.; Smetazko, M.; Saba, M.; Alguel, Y.; Schalkhammer, T., Supported Membrane Nanodevices. *J Nanosci Nanotech* 2004, 4(1/2): 1-22.

Bainbridge, G.; Gokce, I.; Lakey, J. H., Voltage gating is a fundamental feature of porin and toxin beta-barrel membrane channels. *FEBS Lett* 1998, 431(3):305-308.

Bayley, H.; Cremer, P. S., Stochastic sensors inspired by biology. *Nature* 2001, 413(6852):226-230.

Beddow, J. A.; Peterson, I. R.; Heptinstall, J.; Walton, D. J., Reconstitution of nicotinic acetylcholine receptors into gel-protected lipid membranes. *Anal Chem* 2004, 76(8):2261-2265.

Canal, T.; Peppas, N. A., Correlation between mesh size and equilibrium degree of swelling of polymeric networks. *J Biomed Mater Res* 1989, 23(10): 1183-93.

Costello, R. F.; Peterson, I. R.; Heptinstall, J.; Walton, D. J., Improved gel-protected bilayers. *Biosensors Bioelectronics* 1999, 14(3):265-271.

Favero, G.; D'Annibale, A.; Campanella, L.; Santucci, R.; Ferri, T., Membrane supported lipid bilayer membranes array: preparation, stability and ion-channel insertion. *Analytica Chimica Acta* 2002, 460(1):23-34.

Ide, T.; Takeuchi, Y.; Aoki, T.; Yanagida, T., Simultaneous Optical and Electrical Recording of a Single Ion-Channel. *Japanese J Physiol* 2002, 52:429-434.

Ide, T.; Yanagida, T., An Artificial Lipid Bilayer Formed on an Agarose-Coated Glass for Simultaneous Electrical and Optical Measurement of Single Ion Channels. *Biochem Biophys Res Commun* 1999, 265:595-599.

Kasianowicz, J.; Brandin, E.; Branton, D.; Deamer, D. W., Characterization of individual polynucleotide molecules using a membrane channel *Proc Natl Acad Sci USA* 1996, 93, 13770-13773.

Knoll, W.; Frank, C. W.; Heibel, C.; Naumann, R.; Offenhausser, A.; Ruhe, J.; Schmidt, E. K.; Shen, W. W.; Sinner, A., Functional tethered lipid bilayers. *Rev Mol Biotech* 2000, 74(3):137-158.

Krishna, G.; Schulte, J.; Cornell, B. A.; Pace, R. J.; Osman, P. D., Tethered Bilayer Membranes Containing Ionic Reservoirs: Selectivity and Conductance. *Langmuir* 2003, 19:2294-2305.

Kuhner, M.; Tampe, R.; Sackmann, E., Lipid mono- and bilayer supported on polymer films: composite polymer-lipid films on solid substrates. *Biophys J* 1994, 67(1):217-226.

Lee, J. N.; Park, C.; Whitesides, G. M., Solvent compatibility of poly(dimethylsiloxane)-based microfluidic devices. *Anal Chem* 2003, 75(23):6544-6554.

Lu, X.; Ottava, A. L.; Tien, H. T., Biophysical aspects of agar-gel supported bilayer lipid membranes: a new method for forming and studying planar bilayer lipid membranes. *Bioelectrochem Bioenergetics* 1996, 39:285-289.

Lustig, S. R.; Peppas, N. A., Solute Diffusion in Swollen Membranes 0.9. Scaling Laws for Solute Diffusion in Gels. *J Appl Polymer Sci* 1988, 36(4):735-747.

McDonald, J. C.; Whitesides, G. M., Poly(dimethylsiloxane) as a material for fabricating microfluidic devices. *Acct Chem Res* 2002, 35(7):491-499.

Meller, A.; Nivon, L.; Brandin, E.; Golovchenko, J.; Branton, D., Rapid nanopore discrimination between single polynucleotide molecules. *Proc Natl Acad Sci* 2000, 97:1079-1084.

Miller, C., Ion channel reconstitution. ed.; Plenum Press: New York, 1986; p 577.

Mueller, P.; Rudin, D. O.; Tien, H. T.; Wescott, W. C., Reconstitution of cell membrane structure in vitro and its transformation into an excitable system. *Nature* 1962, 194:979-980.

Nakane, J. J.; Akeson, M.; Marziali, A., Nanopore sensors for nucleic acid analysis. *J Phys Condensed Matter* 2003, 15(32):R1365—R1393.

Naumowicz, M.; Figaszewski, Z., Impedance analysis of phosphatidylcholine membranes modified with gramicidin D. *Bioelectrochem* 2003, 61:21-27.

Rehak, M.; Hall, E. A. H., Examination of bilayer lipid membranes for 'pin-hole' character. *The Analyst* 2004, 129:1014-1025.

Sia, S. K.; Whitesides, G. M., Microfluidic devices fabricated in poly(dimethylsiloxane) for biological studies. *Electrophoresis* 2003, 24(21):3563-3576.

Song, H.; Ismagilov, R. F., Millisecond kinetics on a microfluidic chip using nanoliters of reagents. *J Am Chem Soc* 2003, 125(47):14613-14619.

Song, L.; Hobaugh, M. R.; Shustak, C.; Cheley, S.; Bayley, H.; Gouaux, J. E., Structure of staphylococcal alpha-hemolysin, a heptameric transmembrane pore. *Science* 1996, 274 (5294):1859-66.

Terrattaz, S.; Mayer, M.; Vogel, H., Highly Electrically Insulating Tethered Lipid Bilayers for Probing the Function of Ion Channel Proteins. *Langmuir* 2003, 19:5567-5569.

Thorsen, T.; Roberts, R. W.; Arnold, F. H.; Quake, S. R., Dynamic pattern formation in a vesicle-generating microfluidic device. *Phys Rev Lett* 2001, 86(18):4163-4166.

Unger, M. A.; Chou, H. P.; Thorsen, T.; Scherer, A.; Quake, S. R., Monolithic microfabricated valves and pumps by multilayer soft lithography. *Science* 2000, 288(5463), 113-116.

Wang, L. L.; Hosaka, A.; Watanabe, C.; Ohtani, H.; Tsuge, S., Development of a novel solid-phase extraction element for thermal desorption gas chromatography analysis. *J Chrom A* 2004, 1035(2):277-279.

Zheng, B.; Roach, L. S.; Ismagilov, R. F., Screening of protein crystallization conditions on a microfluidic chip using nanoliter-size droplets. *J Am Chem Soc* 2003, 125(37):11170-11171.

What is claimed is:

1. A method of encapsulating a bilayer or monolayer membrane, comprising:
   (a) forming a bilayer or monolayer membrane supported at its boundary by a solid substrate by
      (i) providing a device for preparing a bilayer or monolayer membrane, the device comprising:
         a first channel defined in a first substrate, wherein the first channel contains a first solution;
         a second channel defined in the first substrate or in a second substrate, wherein the second channel contains a second solution;
         wherein the first channel connects to and is in communication with the second channel at an interfacial region defining the connection between the first solution and the second solution; and
         wherein the first channel and/or the second channel comprises a hydrophobic substance at the interfacial region; and
      (ii) introducing a lipid or other amphiphile at the interfacial region,
         wherein the lipid or other amphiphile forms the bilayer or monolayer membrane at the interfacial region by contacting the first solution, the second solution, and the hydrophobic substance; and
   (b) polymerizing a hydrogel prepolymer in the presence of the bilayer or monolayer membrane,
   thereby forming a hydrogel encapsulated bilayer or monolayer membrane supported at its boundary by the solid substrate.

2. The method of claim 1, wherein the lipid or other amphiphile is introduced in an organic solution, wherein the first solution and/or the second solution comprises an aqueous solution, and wherein the bilayer or monolayer membrane formation further comprises
   adjusting the flow of the organic solution and the aqueous solution so that the organic solution forms a droplet in the aqueous solution;
   wherein the organic solution partitions into the hydrophobic substance thereby forming a bilayer or monolayer membrane.

3. The method of claim 1, wherein the hydrogel prepolymer is contacted to the bilayer or monolayer membrane after its formation.

4. The method of claim 1, wherein the hydrogel prepolymer is present before or during the formation of the bilayer or monolayer membrane.

5. The method of claim 1, wherein the bilayer comprises diphytanoylphosphatidylcholine.

6. The method of claim 1, wherein the prepolymer comprises polyethylene oxide or polypropylene oxide.

7. The method of claim 1, wherein the prepolymer comprises hydroxyalkanoates, propylene fumarate, vinylpyrrolidone, vinyl polypyrrolidone, vinyl N-methylpyrrolidone, hydroxypropylcellulose, methylcellulose, sodium alginate, gelatin, acid-hydrolytically-degraded gelatin, agarose, carboxymethylcellulose, carboxypolymethylene, hydroxypropyl methacrylate, hydroxyethyl methacrylate, acrylic acid, acrylamide, N-isopropylacrylamide, N,N-dimethylacrylamide, hyaluronic acid, collagen, or 2-hydroxypropyl methacrylamide.

8. The method of claim 1, wherein the prepolymer comprises polyethyleneglycol-dimethacrylate monomer.

9. The method of claim 1, wherein the hydrogel comprises aminodextran, dextran, DEAE-dextran, chondroitin sulfate, dermatan, heparan, heparin, chitosan, polyethyleneimine, polylysine, dermatan sulfate, heparan sulfate, alginic acid, pectin, carboxymethylcellulose, hyaluronic acid, agarose, carrageenan, starch, polyvinyl alcohol, cellulose, polyacrylic acid, carboxymethyl dextran, polyacrylamide, polyethylene glycol, poly(N-isopropyl acrylamide), poly(hydroxy ethylmethacrylate), polyethylene glycol diacrylate, or combinations thereof.

10. The method of claim 1, wherein the hydrogel comprises polyethylene glycol dimethacrylate.

11. The method of claim 1, wherein the bilayer or monolayer membrane spans a channel of a microfluidic device.

12. The method of claim 1, wherein the first channel and the second channel are both defined in the first substrate.

13. The method of claim 1, wherein the first channel and the second channel are defined in different substrates.

14. The method of claim 1, wherein the first channel comprises a microfluidic channel.

15. The method of claim 1, wherein the second channel comprises a microfluidic channel.

16. The method of claim 1, wherein the first channel and the second channel comprise different portions of the same channel in the first substrate.

17. The method of claim 1, wherein the first channel and the second channel comprise different portions of the same microfluidic channel.

18. The method of claim 1, wherein the first solution comprises water.

19. The method of claim 1, wherein the first solution comprises an aqueous solution.

20. The method of claim 1, wherein the second solution comprises water.

21. The method of claim 1, wherein the second solution comprises an aqueous solution.

22. The method of claim 1, wherein the first solution and the second solution are different.

23. The method of claim 1, wherein introducing is performed with the lipid or other amphiphile in an organic solution, in combination with solvent extraction.

24. The method of claim 1, wherein introducing is performed with the lipid or other amphiphile in an organic solution, the hydrophobic substance being a solvent-absorbing hydrophobic substance.

25. The method of claim 1, wherein the hydrophobic substance is a hydrophobic polymer.

26. The method of claim 1, wherein the hydrophobic substance is PDMS.

* * * * *